(12) United States Patent
Farnan et al.

(10) Patent No.: US 11,694,794 B2
(45) Date of Patent: *Jul. 4, 2023

(54) SYSTEM AND METHOD FOR REDUCTION OF INADVERTENT ACTIVATION OF MEDICAL DEVICE DURING MANIPULATION

(71) Applicant: Tandem Diabetes Care, Inc., San Diego, CA (US)

(72) Inventors: Jason A. Farnan, San Diego, CA (US); Brian Bureson, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/149,559

(22) Filed: May 9, 2016

(65) Prior Publication Data

US 2016/0271325 A1    Sep. 22, 2016

Related U.S. Application Data

(63) Continuation of application No. 13/801,274, filed on Mar. 13, 2013, now Pat. No. 9,335,910.

(Continued)

(51) Int. Cl.
*G16H 40/63* (2018.01)
*G06F 3/04847* (2022.01)
(Continued)

(52) U.S. Cl.
CPC ........ *G16H 40/63* (2018.01); *A61M 5/14244* (2013.01); *G06F 3/0482* (2013.01);
(Continued)

(58) Field of Classification Search
CPC ... G16H 40/63; G16H 20/17; A61M 5/14244; A61M 2005/14208; A61M 2205/12;
(Continued)

(56) References Cited

U.S. PATENT DOCUMENTS 4,810,243 A    3/1989  Howson
5,247,434 A    9/1993  Peterson et al.
(Continued)

FOREIGN PATENT DOCUMENTS

EP    0985420    3/2000
EP    1769812    4/2007
(Continued)

OTHER PUBLICATIONS

US 8,333,733 B2, 12/2012, Lanigan et al. (withdrawn)
(Continued)

*Primary Examiner* — Matthew Ell
*Assistant Examiner* — Kenny Nguyen
(74) *Attorney, Agent, or Firm* — Patterson Thuente. P.A.

(57) ABSTRACT

Inadvertent activation of a portable medical device such as an ambulatory infusion pump can be reduced by locking a touchscreen of the device when it is indicated that an uninterrupted operation is to be performed. When a processor receives a device operation input from the touchscreen that indicates an uninterrupted operation is to be performed on the portable device, the touchscreen is automatically locked such that touch input at the touchscreen is not processed by the processor to navigate between or among menu screens or set pump parameters. Following completion of the uninterrupted operation, the touchscreen can be unlocked. In one embodiment, the touchscreen can be unlocked by selection of an unlock icon on the touchscreen.

16 Claims, 10 Drawing Sheets

Related U.S. Application Data

(60) Provisional application No. 61/637,210, filed on Apr. 23, 2012.

(51) Int. Cl.
*G16H 20/17* (2018.01)
*A61M 5/142* (2006.01)
*G06F 3/04817* (2022.01)
*G06F 3/0482* (2013.01)
*G06F 3/0484* (2022.01)
*G06F 3/04883* (2022.01)

(52) U.S. Cl.
CPC ........ *G06F 3/0484* (2013.01); *G06F 3/04817* (2013.01); *G06F 3/04847* (2013.01); *G06F 3/04883* (2013.01); *G16H 20/17* (2018.01); *A61M 2005/14208* (2013.01); *A61M 2205/12* (2013.01); *A61M 2205/505* (2013.01)

(58) Field of Classification Search
CPC .......... A61M 2205/505; G06F 3/04817; G06F 3/0482; G06F 3/0484; G06F 3/04847; G06F 3/04883
See application file for complete search history.

(56) References Cited

U.S. PATENT DOCUMENTS

| | | | |
|---|---|---|---|
| 5,338,157 A | 8/1994 | Blomquist | |
| 5,485,408 A | 1/1996 | Blomquist | |
| 5,497,772 A | 3/1996 | Schulman et al. | |
| 5,498,421 A | 3/1996 | Grinstaff et al. | |
| 5,558,638 A | 9/1996 | Evers et al. | |
| 5,639,473 A | 6/1997 | Grinstaff et al. | |
| 5,660,163 A | 8/1997 | Schulman et al. | |
| 5,681,285 A | 10/1997 | Ford et al. | |
| 5,685,844 A | 11/1997 | Marttila | |
| 5,707,212 A | 1/1998 | Matthews | |
| 5,728,396 A | 3/1998 | Peery et al. | |
| 5,782,805 A | 7/1998 | Meinzer et al. | |
| 5,830,195 A | 11/1998 | Peters et al. | |
| 5,848,593 A | 12/1998 | Mcgrady et al. | |
| 5,935,099 A | 8/1999 | Peterson et al. | |
| 5,964,724 A | 10/1999 | Rivera et al. | |
| 5,985,305 A | 11/1999 | Peery et al. | |
| 5,988,851 A | 11/1999 | Gent | |
| 6,024,539 A | 2/2000 | Blomquist | |
| 6,039,251 A * | 3/2000 | Holowko | A61M 5/172 235/380 |
| 6,056,522 A | 5/2000 | Johnson | |
| 6,070,761 A | 6/2000 | Bloom et al. | |
| 6,126,642 A | 10/2000 | Kriesel et al. | |
| 6,198,383 B1 | 3/2001 | Sekura et al. | |
| 6,241,704 B1 | 6/2001 | Peterson et al. | |
| 6,269,340 B1 | 7/2001 | Ford et al. | |
| 6,395,292 B2 | 5/2002 | Peery et al. | |
| 6,427,088 B1 | 7/2002 | Bowman, IV et al. | |
| 6,470,234 B1 | 10/2002 | Mcgrady | |
| 6,475,180 B2 | 11/2002 | Peterson et al. | |
| 6,493,745 B1 * | 12/2002 | Cherian | G06F 9/54 709/206 |
| 6,511,435 B1 | 1/2003 | Bluth et al. | |
| 6,551,276 B1 | 4/2003 | Mann et al. | |
| 6,554,798 B1 | 4/2003 | Mann et al. | |
| 6,562,001 B2 | 5/2003 | Lebel et al. | |
| 6,564,105 B2 | 5/2003 | Starkweather et al. | |
| 6,571,128 B2 | 5/2003 | Lebel et al. | |
| 6,577,899 B2 | 6/2003 | Lebel et al. | |
| 6,585,644 B2 | 7/2003 | Lebel et al. | |
| 6,635,014 B2 | 10/2003 | Starkweather et al. | |
| 6,635,048 B1 | 10/2003 | Ullestad et al. | |
| 6,648,821 B2 | 11/2003 | Lebel et al. | |
| 6,659,948 B2 | 12/2003 | Lebel et al. | |
| 6,668,196 B1 | 12/2003 | Villegas et al. | |
| 6,687,546 B2 | 2/2004 | Lebel et al. | |
| 6,694,191 B2 | 2/2004 | Starkweather et al. | |
| 6,733,446 B2 | 5/2004 | Lebel et al. | |
| 6,738,052 B1 | 5/2004 | Manke et al. | |
| 6,740,075 B2 | 5/2004 | Lebel et al. | |
| 6,744,350 B2 | 6/2004 | Blomquist | |
| 6,758,810 B2 | 7/2004 | Lebel et al. | |
| 6,788,315 B1 * | 9/2004 | Kekic | H04L 41/22 715/764 |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,852,104 B2 | 2/2005 | Blomquist | |
| 6,872,200 B2 | 3/2005 | Mann et al. | |
| 6,873,268 B2 | 3/2005 | Lebel et al. | |
| 6,936,029 B2 | 8/2005 | Mann et al. | |
| 6,950,708 B2 | 9/2005 | Bowman, IV et al. | |
| 6,958,705 B2 | 10/2005 | Lebel et al. | |
| 6,974,437 B2 | 12/2005 | Lebel et al. | |
| 6,979,326 B2 | 12/2005 | Mann et al. | |
| 6,990,809 B2 | 1/2006 | Abouraphael | |
| 6,997,920 B2 | 2/2006 | Mann et al. | |
| 7,024,245 B2 | 4/2006 | Lebel et al. | |
| 7,025,743 B2 | 4/2006 | Mann et al. | |
| 7,090,648 B2 | 8/2006 | Sackner et al. | |
| 7,109,878 B2 | 9/2006 | Mann et al. | |
| 7,118,676 B2 | 10/2006 | Mueth et al. | |
| 7,141,425 B2 | 11/2006 | Dzekunov et al. | |
| 7,171,274 B2 | 1/2007 | Starkweather et al. | |
| 7,201,730 B2 | 4/2007 | Davidner et al. | |
| 7,204,823 B2 | 4/2007 | Estes et al. | |
| 7,207,964 B2 | 4/2007 | Davidner et al. | |
| 7,256,771 B2 | 8/2007 | Novak et al. | |
| 7,256,888 B2 | 8/2007 | Staehr et al. | |
| 7,264,730 B2 | 9/2007 | Connell et al. | |
| 7,303,680 B2 | 12/2007 | Connell et al. | |
| 7,318,892 B2 | 1/2008 | Connell et al. | |
| 7,347,819 B2 | 3/2008 | Lebel et al. | |
| 7,347,836 B2 | 3/2008 | Peterson et al. | |
| 7,351,340 B2 | 4/2008 | Connell et al. | |
| 7,369,635 B2 | 5/2008 | Spital et al. | |
| 7,390,314 B2 | 6/2008 | Stutz, Jr. et al. | |
| 7,445,616 B2 | 11/2008 | Petrakis | |
| 7,455,663 B2 | 11/2008 | Bikovsky | |
| 7,471,994 B2 | 12/2008 | Ford et al. | |
| 7,515,060 B2 | 4/2009 | Blomquist | |
| 7,591,801 B2 | 9/2009 | Brauker et al. | |
| 7,630,791 B2 | 12/2009 | Nguyen et al. | |
| 7,651,489 B2 | 1/2010 | Estes et al. | |
| 7,654,976 B2 | 2/2010 | Peterson et al. | |
| 7,678,071 B2 | 3/2010 | Lebel et al. | |
| 7,682,338 B2 | 3/2010 | Griffin | |
| 7,699,767 B2 | 4/2010 | Mueth et al. | |
| 7,713,574 B2 | 5/2010 | Brister et al. | |
| 7,717,903 B2 | 5/2010 | Estes et al. | |
| 7,736,338 B2 | 6/2010 | Kavazov et al. | |
| 7,774,145 B2 | 8/2010 | Brauker et al. | |
| 7,778,680 B2 | 8/2010 | Goode, Jr. et al. | |
| 7,789,857 B2 | 9/2010 | Moberg et al. | |
| 7,797,028 B2 | 9/2010 | Goode, Jr. et al. | |
| 7,801,596 B2 | 9/2010 | Fischell et al. | |
| 7,811,279 B2 | 10/2010 | John | |
| 7,815,602 B2 | 10/2010 | Mann et al. | |
| 7,819,843 B2 | 10/2010 | Mann et al. | |
| 7,828,528 B2 | 11/2010 | Estes et al. | |
| 7,831,310 B2 | 11/2010 | Lebel et al. | |
| 7,837,647 B2 | 11/2010 | Estes et al. | |
| 7,837,651 B2 | 11/2010 | Bishop et al. | |
| 7,875,022 B2 | 1/2011 | Wenger et al. | |
| 7,912,674 B2 | 3/2011 | Killoren Clark et al. | |
| 7,914,450 B2 | 3/2011 | Goode, Jr. et al. | |
| 7,925,321 B2 | 4/2011 | Goode et al. | |
| 7,933,639 B2 | 4/2011 | Goode et al. | |
| 7,933,780 B2 | 4/2011 | De La Huerga | |
| 7,938,792 B2 | 5/2011 | Roger et al. | |
| 7,955,261 B2 | 6/2011 | Goode et al. | |
| 7,957,984 B1 | 6/2011 | Vallone | |
| 7,959,569 B2 | 6/2011 | Goode et al. | |

(56) References Cited

U.S. PATENT DOCUMENTS

| | | |
|---|---|---|
| 7,963,954 B2 | 6/2011 | Kavazov |
| 7,972,296 B2 | 7/2011 | Braig et al. |
| 7,976,492 B2 | 7/2011 | Brauker et al. |
| 7,976,530 B2 | 7/2011 | Johnson et al. |
| 7,976,778 B2 | 7/2011 | Drucker et al. |
| 7,979,104 B2 | 7/2011 | Kamath et al. |
| 7,986,986 B2 | 7/2011 | Goode et al. |
| 7,988,674 B2 | 8/2011 | Adams et al. |
| 7,988,849 B2 | 8/2011 | Biewer et al. |
| 8,002,700 B2 | 8/2011 | Ferek-Petric et al. |
| 8,012,119 B2 | 9/2011 | Estes et al. |
| 8,020,564 B2 | 9/2011 | Batch |
| 8,034,019 B2 | 10/2011 | Nair et al. |
| 8,034,026 B2 | 10/2011 | Grant et al. |
| 8,052,601 B2 | 11/2011 | Goode, Jr. et al. |
| 8,066,197 B2 | 11/2011 | Sheppard |
| 8,094,009 B2 | 1/2012 | Allen et al. |
| 8,109,921 B2 | 2/2012 | Estes et al. |
| 8,130,095 B2 | 3/2012 | Allen et al. |
| 8,147,446 B2 | 4/2012 | Yodfat et al. |
| 8,206,350 B2 | 6/2012 | Mann et al. |
| 8,211,364 B2 | 7/2012 | Drucker et al. |
| 8,221,359 B2 | 7/2012 | Kristensen et al. |
| 8,236,242 B2 | 8/2012 | Drucker et al. |
| 8,250,483 B2 | 8/2012 | Blomquist |
| 8,257,652 B2 | 9/2012 | Drucker et al. |
| 8,257,653 B2 | 9/2012 | Drucker et al. |
| 8,267,921 B2 | 9/2012 | Yodfat et al. |
| 8,290,562 B2 | 10/2012 | Goode, Jr. et al. |
| 8,310,415 B2 | 11/2012 | Mclaughlin et al. |
| 8,323,188 B2 | 12/2012 | Tran |
| 8,332,008 B2 | 12/2012 | Goode et al. |
| 8,344,847 B2 | 1/2013 | Moberg et al. |
| 8,346,399 B2 | 1/2013 | Blomquist |
| 8,369,919 B2 | 2/2013 | Kamath et al. |
| 8,390,244 B2 | 3/2013 | Wooley et al. |
| 8,395,581 B2 | 3/2013 | Gråskov et al. |
| 8,401,194 B2 | 3/2013 | Nierzwick et al. |
| 8,414,563 B2 | 4/2013 | Kamen et al. |
| 8,449,523 B2* | 5/2013 | Brukalo ............ A61M 5/14244 |
| | | 604/504 |
| 8,449,524 B2 | 5/2013 | Braig et al. |
| 8,451,230 B2 | 5/2013 | Celentano et al. |
| 8,460,231 B2 | 6/2013 | Brauker et al. |
| 8,504,842 B1 | 8/2013 | Meacham |
| 8,579,853 B2 | 11/2013 | Reggiardo et al. |
| 8,601,465 B2 | 12/2013 | Bernstein |
| 8,868,794 B2 | 10/2014 | Masoud |
| 8,893,053 B1 | 11/2014 | Hyde et al. |
| 8,929,823 B2* | 1/2015 | Mears .................. A61B 5/0002 |
| | | 455/41.2 |
| 8,932,250 B2* | 1/2015 | Montgomery ......... G16H 40/67 |
| | | 604/67 |
| 8,963,855 B2 | 2/2015 | Chen et al. |
| 8,992,475 B2 | 3/2015 | Mann |
| 9,132,227 B2 | 9/2015 | Bryant, Jr. |
| 9,137,301 B1* | 9/2015 | Dunlap ............... H04L 67/1021 |
| 9,238,100 B2 | 1/2016 | Kruse et al. |
| 9,259,531 B2 | 2/2016 | Kamen |
| 9,335,910 B2 | 5/2016 | Farnan et al. |
| 9,715,327 B2 | 7/2017 | Rosinko et al. |
| 11,217,339 B2* | 1/2022 | Blomquist ........ A61M 5/14244 |
| 2001/0031944 A1* | 10/2001 | Peterson ............ A61M 5/14228 |
| | | 604/65 |
| 2002/0029776 A1 | 3/2002 | Blomquist |
| 2002/0078393 A1 | 6/2002 | Parker |
| 2002/0143290 A1 | 10/2002 | Bui et al. |
| 2002/0183693 A1 | 12/2002 | Peterson et al. |
| 2003/0065308 A1 | 4/2003 | Lebel et al. |
| 2003/0163088 A1 | 8/2003 | Blomquist |
| 2003/0163223 A1 | 8/2003 | Blomquist |
| 2003/0163789 A1 | 8/2003 | Blomquist |
| 2003/0195974 A1* | 10/2003 | Ronning .................. G06F 8/65 |
| | | 709/230 |

| | | |
|---|---|---|
| 2003/0212364 A1 | 11/2003 | Mann et al. |
| 2004/0073095 A1 | 4/2004 | Causey et al. |
| 2004/0193090 A1 | 9/2004 | Lebel et al. |
| 2005/0022274 A1 | 1/2005 | Campbell et al. |
| 2005/0143864 A1 | 6/2005 | Blomquist |
| 2005/0160084 A1 | 7/2005 | Barrett |
| 2005/0171513 A1 | 8/2005 | Mann et al. |
| 2006/0173444 A1 | 8/2006 | Choy et al. |
| 2006/0229557 A1 | 10/2006 | Fathallah |
| 2007/0093786 A1 | 4/2007 | Goldsmith et al. |
| 2007/0118405 A1 | 5/2007 | Campbell et al. |
| 2007/0156033 A1 | 7/2007 | Causey et al. |
| 2007/0219480 A1 | 9/2007 | Kamen et al. |
| 2007/0219496 A1 | 9/2007 | Kamen et al. |
| 2007/0219597 A1 | 9/2007 | Kamen et al. |
| 2007/0228071 A1 | 10/2007 | Kamen et al. |
| 2007/0287985 A1 | 12/2007 | Estes et al. |
| 2008/0033357 A1 | 2/2008 | Mann et al. |
| 2008/0065007 A1 | 3/2008 | Peterson et al. |
| 2008/0065016 A1 | 3/2008 | Peterson et al. |
| 2008/0119705 A1 | 5/2008 | Patel et al. |
| 2008/0122595 A1 | 5/2008 | Yamamichi et al. |
| 2008/0147004 A1 | 6/2008 | Mann et al. |
| 2008/0147050 A1 | 6/2008 | Mann et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0287922 A1 | 11/2008 | Panduro |
| 2008/0312584 A1* | 12/2008 | Montgomery ......... G16H 20/17 |
| | | 604/67 |
| 2008/0312585 A1* | 12/2008 | Brukalo ................ G16H 20/17 |
| | | 604/67 |
| 2009/0005729 A1* | 1/2009 | Hendrixson ....... G05B 19/0428 |
| | | 604/67 |
| 2009/0018495 A1 | 1/2009 | Panduro |
| 2009/0037020 A1 | 2/2009 | Brown |
| 2009/0067989 A1 | 3/2009 | Estes et al. |
| 2009/0069745 A1 | 3/2009 | Estes et al. |
| 2009/0082728 A1 | 3/2009 | Bikovsky |
| 2009/0085768 A1 | 4/2009 | Patel et al. |
| 2009/0101549 A1 | 4/2009 | Kamen et al. |
| 2009/0107335 A1 | 4/2009 | Wilt et al. |
| 2009/0108016 A1 | 4/2009 | Brown et al. |
| 2009/0156990 A1 | 6/2009 | Wenger et al. |
| 2009/0192724 A1 | 7/2009 | Brauker et al. |
| 2009/0212966 A1 | 8/2009 | Panduro |
| 2009/0221890 A1 | 9/2009 | Saffer et al. |
| 2009/0254037 A1 | 10/2009 | Bryant, Jr. et al. |
| 2009/0270833 A1 | 10/2009 | Debelser et al. |
| 2010/0069890 A1 | 3/2010 | Gräskov et al. |
| 2010/0107103 A1 | 4/2010 | Wallaert et al. |
| 2010/0121169 A1 | 5/2010 | Petisce et al. |
| 2010/0145262 A1 | 6/2010 | Bengtsson et al. |
| 2010/0152674 A1 | 6/2010 | Kavazov et al. |
| 2010/0156633 A1* | 6/2010 | Buck, Jr. ........... A61M 5/14244 |
| | | 340/540 |
| 2010/0168543 A1 | 7/2010 | Kamath et al. |
| 2010/0179402 A1 | 7/2010 | Goode, Jr. et al. |
| 2010/0198183 A1 | 8/2010 | Lanigan et al. |
| 2010/0228146 A1 | 9/2010 | Estes et al. |
| 2010/0256047 A1* | 10/2010 | Sieh ......................... A61P 3/10 |
| | | 514/5.9 |
| 2010/0257490 A1* | 10/2010 | Lyon ..................... H04M 1/724 |
| | | 715/863 |
| 2010/0261987 A1 | 10/2010 | Kamath et al. |
| 2010/0272452 A1* | 10/2010 | Tsukijima .......... G03G 21/1633 |
| | | 399/27 |
| 2010/0292556 A1 | 11/2010 | Golden |
| 2010/0312082 A1 | 12/2010 | Batman et al. |
| 2010/0318578 A1* | 12/2010 | Treu ....................... G16H 20/00 |
| | | 707/802 |
| 2010/0331824 A1 | 12/2010 | Moberg et al. |
| 2011/0006876 A1 | 1/2011 | Moberg et al. |

(56) References Cited

U.S. PATENT DOCUMENTS

| | | | |
|---|---|---|---|
| 2011/0006880 A1* | 1/2011 | Long | A61B 5/1172 340/5.83 |
| 2011/0009724 A1* | 1/2011 | Hill | A61B 5/002 600/365 |
| 2011/0009725 A1* | 1/2011 | Hill | A61B 5/150022 600/365 |
| 2011/0009813 A1* | 1/2011 | Rankers | A61B 5/15087 604/66 |
| 2011/0030845 A1 | 2/2011 | Chong et al. | |
| 2011/0040247 A1* | 2/2011 | Mandro | A61M 5/14244 604/66 |
| 2011/0047499 A1 | 2/2011 | Mandro et al. | |
| 2011/0053121 A1 | 3/2011 | Heaton | |
| 2011/0071465 A1 | 3/2011 | Wang et al. | |
| 2011/0081889 A1* | 4/2011 | Gao | G06F 3/038 455/411 |
| 2011/0082439 A1 | 4/2011 | Wenger et al. | |
| 2011/0092894 A1 | 4/2011 | Mcgill et al. | |
| 2011/0098637 A1 | 4/2011 | Hill | |
| 2011/0098638 A1 | 4/2011 | Chawla et al. | |
| 2011/0098674 A1 | 4/2011 | Vicente et al. | |
| 2011/0105854 A1 | 5/2011 | Kiani et al. | |
| 2011/0106318 A1 | 5/2011 | Ledford | |
| 2011/0119087 A1 | 5/2011 | Drucker et al. | |
| 2011/0125085 A1 | 5/2011 | Mcgill et al. | |
| 2011/0125095 A1 | 5/2011 | Lebel et al. | |
| 2011/0125530 A1 | 5/2011 | Drucker et al. | |
| 2011/0126188 A1 | 5/2011 | Bernstein et al. | |
| 2011/0133946 A1 | 6/2011 | Kopp et al. | |
| 2011/0137239 A1 | 6/2011 | Debelser et al. | |
| 2011/0144586 A1* | 6/2011 | Michaud | F16J 15/32 604/151 |
| 2011/0152770 A1 | 6/2011 | DiPerna et al. | |
| 2011/0178461 A1 | 7/2011 | Chong et al. | |
| 2011/0184264 A1 | 7/2011 | Galasso et al. | |
| 2011/0190614 A1 | 8/2011 | Brister et al. | |
| 2011/0190694 A1 | 8/2011 | Lanier, Jr. et al. | |
| 2011/0208123 A1 | 8/2011 | Gray et al. | |
| 2011/0256024 A1 | 10/2011 | Cole et al. | |
| 2011/0257895 A1 | 10/2011 | Brauker et al. | |
| 2012/0030610 A1 | 2/2012 | DiPerna et al. | |
| 2012/0041415 A1 | 2/2012 | Estes et al. | |
| 2012/0084728 A1* | 4/2012 | Huang | G06F 3/0416 715/810 |
| 2012/0093311 A1* | 4/2012 | Nierzwick | H04W 12/50 380/255 |
| 2012/0095315 A1 | 4/2012 | Tenbarge et al. | |
| 2012/0095393 A1* | 4/2012 | Reinke | G16H 40/63 604/66 |
| 2012/0109100 A1 | 5/2012 | Estes et al. | |
| 2012/0130204 A1 | 5/2012 | Basta et al. | |
| 2012/0185267 A1* | 7/2012 | Kamen | A61B 5/0024 705/2 |
| 2012/0232520 A1 | 9/2012 | Sloan et al. | |
| 2012/0238851 A1* | 9/2012 | Kamen | A61M 5/14244 600/365 |
| 2012/0266251 A1* | 10/2012 | Birtwhistle | H04W 12/08 726/26 |
| 2012/0307126 A1 | 12/2012 | Bhogal | |
| 2013/0050106 A1 | 2/2013 | Chung et al. | |
| 2013/0117696 A1* | 5/2013 | Robertson | G16H 15/00 715/763 |
| 2013/0137415 A1* | 5/2013 | Takikawa | H04W 4/48 455/418 |
| 2013/0171938 A1* | 7/2013 | Mears | G16H 40/67 455/41.2 |
| 2013/0172710 A1 | 7/2013 | Mears et al. | |
| 2013/0190094 A1* | 7/2013 | Ronen | A63F 13/79 463/42 |
| 2013/0191770 A1* | 7/2013 | Bartz | G16H 20/17 715/771 |
| 2013/0283196 A1 | 10/2013 | Farnan et al. | |
| 2013/0332874 A1 | 12/2013 | Rosinko et al. | |
| 2013/0345625 A1 | 12/2013 | Causey, III et al. | |
| 2014/0012511 A1 | 1/2014 | Mensinger et al. | |
| 2014/0054883 A1 | 2/2014 | Lanigan et al. | |
| 2014/0180711 A1 | 6/2014 | Kamen et al. | |
| 2014/0276531 A1 | 9/2014 | Walsh | |
| 2014/0323961 A1 | 10/2014 | Blomquist et al. | |
| 2015/0072613 A1 | 3/2015 | Swanson | |
| 2015/0182694 A1 | 7/2015 | Rosinko | |
| 2015/0182695 A1 | 7/2015 | Rosinko | |
| 2015/0217044 A1 | 8/2015 | Blomquist | |
| 2016/0121047 A1 | 5/2016 | Kruse et al. | |
| 2016/0199571 A1 | 7/2016 | Rosinko et al. | |
| 2016/0271325 A1 | 9/2016 | Farnan et al. | |
| 2017/0300206 A1 | 10/2017 | Rosinko et al. | |

FOREIGN PATENT DOCUMENTS

| | | |
|---|---|---|
| EP | 2079011 | 7/2009 |
| WO | WO 9524229 A2 | 9/1995 |
| WO | WO 0018449 A2 | 4/2000 |
| WO | WO03008014 | 1/2003 |
| WO | WO2008127694 A1 | 10/2008 |
| WO | WO2009032399 A1 | 3/2009 |
| WO | WO2009032400 A1 | 3/2009 |
| WO | WO2011005633 | 1/2011 |

OTHER PUBLICATIONS

Title: Introduction to Windows in DOC. Publisher: Imperial college london. Publication date: Feb. 28, 2011. URL: http://web.archive.org/web/20110228233235/https://www.doc.ic.ac.uk/csg-old/windows/intro.html.*

Search Report for EP Application No. 13781696.3 dated Nov. 25, 2015.

Search Report and Written Opinion dated Jul. 29, 2013 for PCT Application No. PCT/US-2013/037616 filed Apr. 22, 2013, 10 pages.

Written Opinion dated Oct. 28, 2014 for PCT Application No. PCT/US-2013/037616 filed Apr. 22, 2013, 6 pages.

Application and File History for U.S. Appl. No. 13/801,230, filed Mar. 13, 2013, inventor Rosinko et al.

PCT Search Report dated Sep. 4, 2013 for PCT Application No. PCT/US-2013/0044329 filed Jun. 13, 2013, 13 pages.

Communication dated Jun. 6, 2017 for EP Application No. 13800236.5. (9 pages).

IPRP for International PCT Application No. PCT/US-2013/0044329 dated Dec. 9, 2014.

Exam Report for European Application No. 13781696.3 dated Jan. 3, 2017.

Application and File History for U.S. Appl. No. 13/801,274, filed Mar. 13, 2013, inventors Farnan et al.

Application and File History for U.S. Appl. No. 15/592,595, filed May 11, 2017, inventors Rosinko et al.

Search Report dated Jun. 24, 2019 for EP Application No. 18211743.2, 11 pages.

* cited by examiner

SYSTEM AND METHOD FOR REDUCTION OF INADVERTENT ACTIVATION OF MEDICAL DEVICE DURING MANIPULATION

RELATED APPLICATIONS

This application is a continuation of application Ser. No. 13/801,274 filed Mar. 13, 2013, which claims the benefit of U.S. Provisional Application No. 61/637,210 filed Apr. 23, 2012, each of which is fully incorporated herein in its entirety by reference.

BACKGROUND

Many portable devices include a touchscreen on which symbols are displayed and from which inputs are received for operation of the portable device. A series of screens or windows can displayed on the touchscreen, showing alphanumeric text and symbols and providing menu screens through which the user can control operation of the portable device. User interaction, such as by touching the alphanumeric text and symbols, provides user input and facilitates navigation through the menu screens and selection of the device functions. Under some conditions, it is desirable to ignore user interaction with the touchscreen. For example, when the portable device is placed in a pocket or a purse, physical contact from objects in the pocket or purse may cause inadvertent device operation to occur. In such conditions, the touchscreen may be placed in a lock condition. The user is then required to perform a particular interaction to resume acceptance of device input through the touchscreen.

One example of a portable device such as described above is a device that involves the delivery of fluids. There are many applications in academic, industrial, and medical fields, as well as others, that involve devices that are capable of accurately and controllably delivering fluids, including liquids and gases, that have a beneficial effect when administered in known and controlled quantities. This is particularly true in the medical field where treatments for many patients include the administration of a known amount of a substance at predetermined intervals. The treatment of diabetes involves just such a regimented dosage of medicament such as insulin. In addition, the administration of insulin for a diabetic patient is one of a few medical indications in which the patient routinely administers the medicament to themselves by a subcutaneous modality, such as a hypodermic syringe injection. As such, providing a patient with the means to safely, reliably, and comfortably administer required doses of medication is particularly important in order to facilitate patient compliance and accurate treatment of the condition.

Insulin infusion pumps have been developed for the administration of insulin for those diagnosed with both type I and type II diabetes. Insulin pumps are medical infusion devices used for the administration of insulin in the treatment of diabetes that offer an alternative to multiple daily injections of insulin by an insulin syringe or an insulin pen. They also allow for continuous insulin therapy.

The functions performed by infusion pumps and similar devices make it especially important to avoid inadvertent device operation. For example, infusion pumps may be programmed to initiate delivery of fluids at different times of a day, but such delivery would be annoying or even dangerous if a user happens to be involved in replacing a cartridge or changing a tube at the time of the programmed delivery time. Such load sequences of operation should not be interrupted until completion. Relatively simple display lock protections may not be adequate to protect against programmed device operation when a user is engaging in an activity that should not be interrupted.

Accordingly, there is a need for a portable medical device that safely facilitates user interaction while in a particular mode in which device activation could be problematic.

SUMMARY

Inadvertent activation of a portable medical device such as an ambulatory infusion pump can be reduced by locking a touchscreen of the device when it is indicated that an uninterrupted operation is to be performed. When a processor receives a device operation input from the touchscreen that indicates an uninterrupted operation is to be performed on the portable device, the touchscreen is automatically locked such that touch input at the touchscreen is not processed by the processor to navigate between or among menu screens or set pump parameters. Following completion of the uninterrupted operation, the touchscreen can be unlocked. In one embodiment, the touchscreen can be unlocked by selection of an unlock icon on the touchscreen.

In an embodiment, an ambulatory infusion pump includes a housing, a delivery mechanism adapted to facilitated delivery of fluid to a user and a user interface comprising a touchscreen. A processor can be configured to generate menu screens for display on the touchscreen and to receive and process touch input from the touchscreen for navigation between or among the menu screens and for setting pump parameters. The processor can further be configured to receive touch input through the user interface that indicates an uninterrupted operation is to be performed on the pump. In response to this touch input, the processor can automatically locked the touch screen to prevent navigation between or among the menu screens or setting of pump parameters. Following completion of the uninterrupted operation, the touchscreen can be unlocked.

In some embodiments, inadvertent activation is reduced by generating a plurality of menu screens for display on a touchscreen of the portable device. The processor can receive a device operation input from the touchscreen that indicates an uninterrupted operation is to be performed on the portable device. The processor responds by setting a state of the portable device that is associated with the device operation input, maintaining the set state until at least a first predetermined touch input and a second predetermined touch input that are separated in time and each associated with a different corresponding first and second predetermined menu screen are received at the processor from the touchscreen. The processor only permits navigation from the first predetermined menu screen to the second predetermined menu screen in response to the first predetermined touch input, and the processor responds to the second predetermined touch input by changing the state of the portable device. Limiting the user interaction in this way can increase the device safety by permitting user interaction only in the sequence from the first predetermined menu screen to the second predetermined menu screen for a particular operating mode.

In an embodiment, a portable device includes a housing, a touchscreen having a surface on which a plurality of menu screens are displayed and from which touch input is received, and a processor in the housing configured to generate menu screens for display on the touchscreen and to receive the touch input from the touchscreen for navigation among the menu screens. The processor responds to receipt of a device operation input that indicates an uninterrupted operation is to be performed on the device by setting a state of the portable device that is associated with the device operation input and maintaining the set state until at least a first predetermined touch input and a second predetermined touch input that are separated in time and each associated with a different corresponding first and second predetermined menu screen, are received from the touchscreen. The processor only permits navigation from the first predetermined menu screen to the second predetermined menu screen in response to the first predetermined touch input, and the processor responds to the second predetermined touch input by changing the state of the portable device.

Other features and advantages of the present invention should be apparent from the following description of preferred embodiments that illustrate, by way of example, the principles of the invention.

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

DETAILED DESCRIPTION

Disclosed herein are embodiments directed to a portable medical device having an interactive, e.g., touch, display screen that automatically locks when the system is in a load sequence which changes the physical state of the device.

Figure 1:
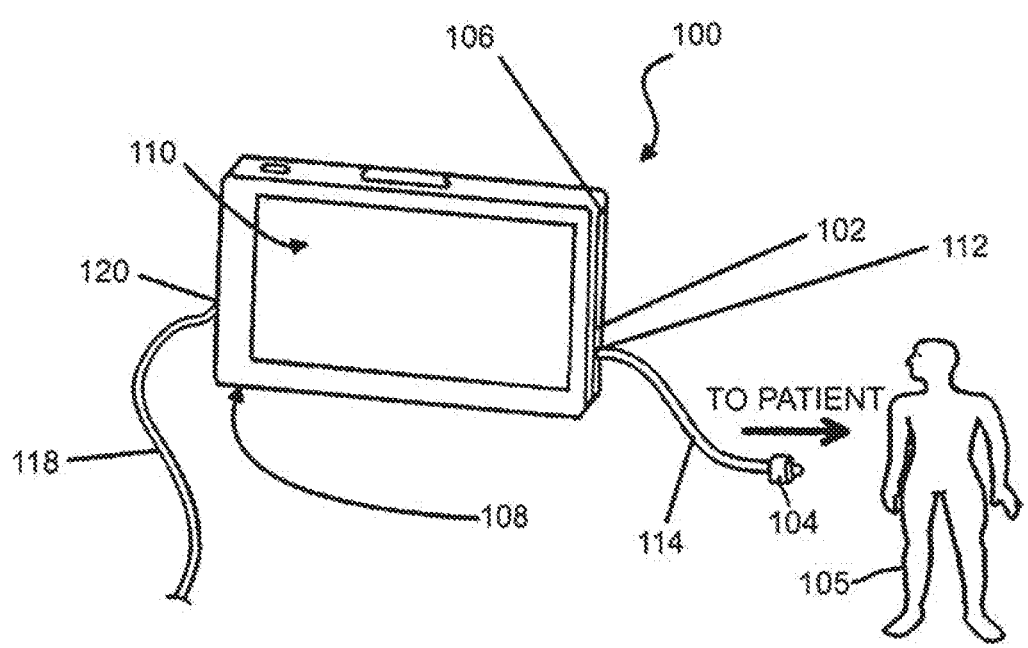
FIG. 1 depicts a portable medical device including an interactive screen element such as a touchscreen in one embodiment.
Figure 2:
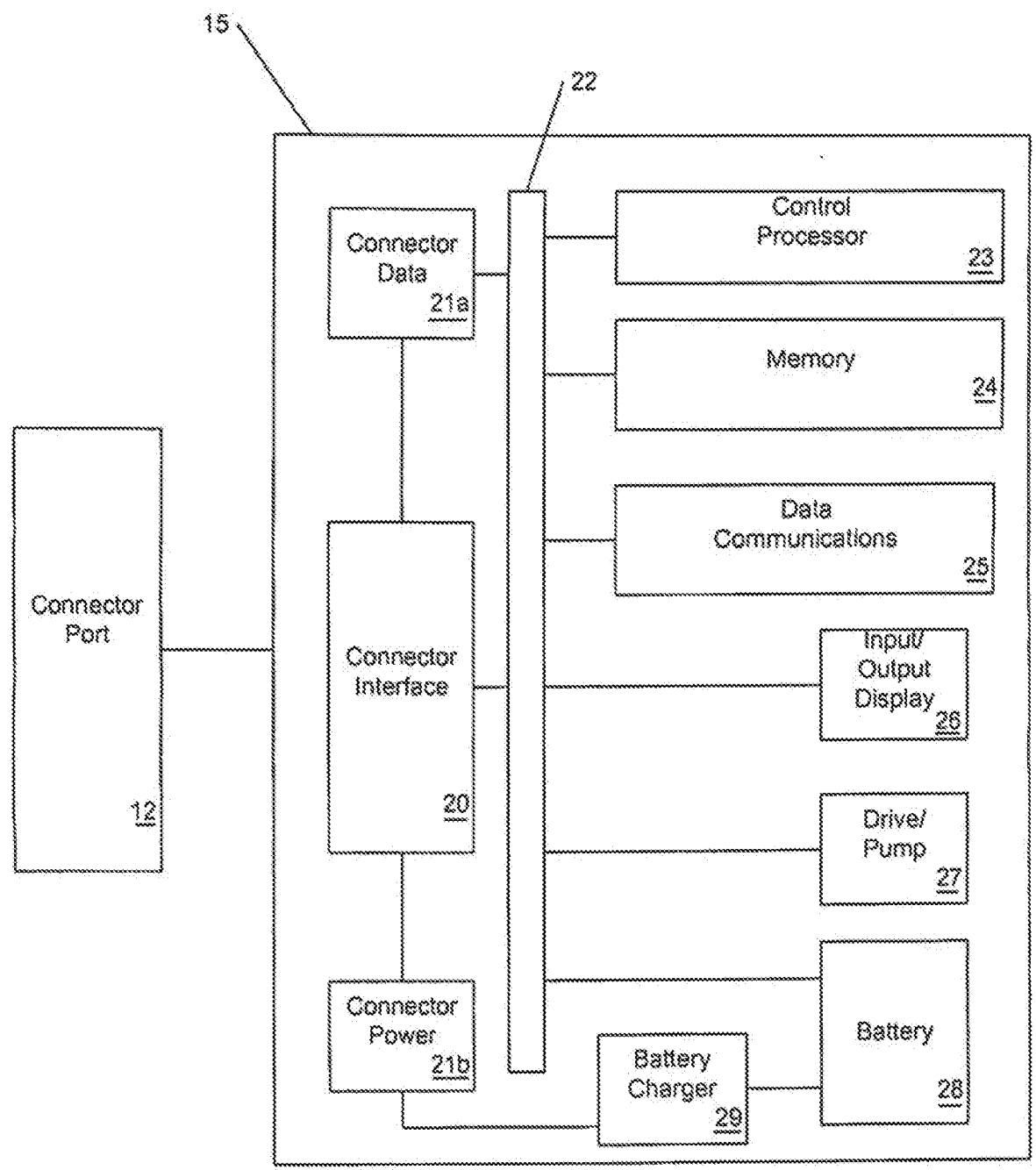
FIG. 2 is a block diagram that illustrates components of the portable medical device of FIG. 1.

Referring to FIG. 1, a schematic representation of a portable medical device 100 for delivering a quantity of fluid to a body is shown. FIG. 2 shows a block diagram of some of the components in the portable medical device 100. In some embodiments, the portable medical device may comprise a portable infusion device for the delivery of insulin or other medicament, such as the infusion pump devices discussed above. Exemplary ambulatory medical devices and features include those, e.g., disclosed in U.S. patent application Ser. No. 13/557,163, U.S. patent application Ser. No. 12/714,299, U.S. patent application Ser. No. 12/538,018, U.S. Provisional Patent Application No. 61/655,883, U.S. Provisional Patent Application No. 61/656,967 and U.S. Pat. No. 8,287,495. Each of the aforementioned documents is hereby incorporated herein by reference in its entirety.

The portable device 100 can include an infusion cartridge 102 having an infusion set connector 104 for connection to a patient 105, and optionally a glucose meter (not illustrated). The infusion cartridge 102 can be functionally and interchangeably inserted into a receiving slot 106 in a housing 108 of the portable infusion pump device 100. The portable device includes a touchscreen 110 on which alphanumeric text, symbols, menu screens, data, and the like can be displayed, and from which user input may be received via interaction such as by pressing the outer surface of the touchscreen. The type of output/display may vary as may be useful for particular application, such as LCD displays, LED displays, plasma displays, OLEO displays, organic LED (OLED) displays, and the like. The touchscreen 110 may be implemented with a capacitance screen, a resistive screen, or other such display/input technology. The portable device 100 may additionally include a keyboard or other input device known in the art for data entry, which may be separate from the display. The device may also include a capability to operatively couple via a wired or wireless (e.g., infrared, electronic, optical, etc.) link to one or more other devices, locally or via a network, such as, e.g., a portable or non-portable medical device, a control unit, external monitor or display, a personal laptop, tablet or mainframe computer, or mobile communication device such as a smartphone or personal digital assistant (PDA), or the like. Such other devices may control or be controlled by device 100 and/or may otherwise communicate for the transfer of data between or among device 100 and other device(s) for analysis of data (e.g., user data for physician review, device diagnostic data for troubleshooting or repair), programming, or other uses.

The infusion cartridge 102 can have an outlet 112 that is coupled to an infusion tube 114 and the infusion set connector 104. The tube 114 and connector 104 comprise an infusion circuit that delivers medicament to the patient 105 at programmed times and in response to manually initiated delivery.

The housing 108 of the infusion pump device 100 can be configured to have any suitable shape and size. For instance, the housing 108 may be substantially planar, or may be extended and tubular, or may be in the shape of a square, rectangle, circle, ellipse cylinder or the like. The housing 108 can be dimensioned so as to be comfortably associated with a user and/or hidden from view, for instance, placed within the clothing of a user or within a case or sleeve. For some embodiments, the housing of the pump device can have a width of about 2.5 inches to about 3.5 inches, a height of about 1.0 inch to about 2.0 inches and a thickness of about 0.2 inches to about 0.6 inches. The materials of the housing 108 can vary as well. In some embodiments, the housing may be constructed as a water-tight, or water-resistant plastic, metallic or composite housing that is glued or otherwise fastened together permanently or semi-permanently.

A unique complication can occur for diabetic users in that they often build up calluses on the tips of their fingers as a result of blood glucose testing, which may be problematic for operation of capacitive-based touch screen configurations. For example, calluses may prevent or hinder the transfer of energy that the capacitive screens use to receive input. Accordingly, in certain embodiments, the touchscreen may be a resistive-based touchscreen. The touchscreen, or touch-sensitive display, may be configured to display menu screens or pages that allow the user to input data fields, e.g., select variable inputs, so as to allow the program to produce a suggested delivery amount, rate, profile, and/or the like in an intuitive, manipulatable and/or graphic representation. The user can therefore interact with the screen to shape the characteristic/form of the delivery amount, rate, and/or graphic delivery profile, e.g., by manipulating the delivery estimate or pattern displayed on the screen to effectuate the actual delivery. The portable infusion device may additionally include a keyboard or other device known in the art for data entry. Such data entry may be separate from the screen and/or display.

Information provided by the portable infusion device may be presented on the display screen as any number of objects, including one or more numeric and/or alphanumeric values, a range, a value or range that is presented in the form of a drop-down menu, a toggle that can be adjusted by the user, a graphical representation (e.g., icon) or an animated graphic, for example. In certain embodiments, the value is a range of values that are presented on a screen of the display as a toggle, wherein the toggle may be adjusted upwards or downwards by the user wiping a finger over the screen to select the appropriate value range, e.g. appropriate range of amounts of medicament such as insulin to be delivered and/or the appropriate rate, time, or interval of medicament delivery. In certain instances, the values presented in the range may be adjusted by the processor (illustrated in FIG. 2).

An infusion workflow, or protocol, may be at least part of a program that is executed by the processor to display a sequence of menu pages to assist a user to at least program or control the portable infusion device and/or at least one operation comprising input, change, confirm, or view various information within the device. Any part of a workflow or protocol may include any number of queries for prompting the user to enter, modify, or confirm information can be presented to the user on the touchscreen display.

For example, a program accessible by the processor that includes an infusion workflow or protocol may enable a user to program the portable infusion device to deliver insulin to the user. In addition, an infusion workflow may present the user with a number of understandable queries enabling the user to enter, confirm, or modify information regarding the physiological conditions of the user. For instance, the menu pages may present a series of queries to a user during the execution of a program and may enable a user to set various settings within the portable infusion device (e.g., the time, date, or one or more alarms) and/or enter information about the user's present or predicted conditions (e.g., blood glucose level, physiological conditions, food to be ingested, and the like). In general, the sequence of menu pages may comprise a linear flow in that each menu page provides an icon or symbol that initiates a next step or menu page in the workflow and also provides an icon or symbol that reverses the workflow to proceed to a preceding menu page in the workflow.

In some embodiments, the user is provided with a virtual form displayed on the touch screen display for the user to complete. A virtual form enables a user to directly select and manipulate one or more parts of a displayed virtual form, with each part generally representing a setting. In this way, a user is not required to navigate through a generally linear workflow or protocol and/or prompted with a series of queries. Instead, the user is presented with a single page where the user completes the virtual form in order to initiate a programmed delivery of insulin, as will be discussed in greater detail below and shown by way of example in FIGS. 3A-3C (with corresponding screenshots in FIGS. 4-11) and FIGS. 12A-12B (with corresponding screenshots in FIGS. 13-16).

Some menu page or screen representation embodiments of the menu page workflow enable a user to easily access and view one or more settings and information within the portable infusion device. A single page may include one or more objects simultaneously presented on the touch screen, where an object may be any number of text, numbers, graphs, pictures, video, or combination thereof which display information to a user.

The settings and information may have been entered by a user and/or presented by the portable infusion device, and may be one of information regarding the amount of insulin already present in the body, e.g., insulin on board; blood glucose level; trending glucose level; insulin sensitivity/insensitivity; glycemic index; metabolism; metabolic rate; stress level; physiological conditions, e.g., age, health, sickness, diurnal cycles, etc; measurable parameters: hormones, steroids, etc.; pharmacokinetics of the medicament, e.g., age of insulin, decay rate, etc.; food to be ingested, e.g., carbohydrates, proteins, fat; activity; use history; calendared events; environment, e.g., temperature, humidity, pressure, etc.; and the like. An object may represent any information without departing from the scope herein, and may also be in the form of a pictogram to generally intuitively represent a program, file, user, setting, status, profile, action, combination of the foregoing, or other entity or combination of entities discussed herein.

FIG. 1 shows an embodiment wherein the portable medical device 100 can be coupled to a power source, such as a desktop or laptop computer or a wall outlet, through a cable 118. The cable connector may comprise, for example, a connector through which both data and electrical energy are received, such as when the device is coupled to a computing device. Examples of such combined power and data cables include a Universal Serial Bus (USB) connection, an IEEE 1499 (FireWire) connection, a "Thunderbolt" connection, PCI Express, eSATA and Ethernet. The port may comprise, for example, a standard USB port, a mini-USB port, a microUSB port, IEEE 1394 (i.e., FIREWIRE, registered to Apple, Inc., Cupertino, Calif.) port, or port for THUNDERBOLT (registered to Apple, Inc., Cupertino, Calif.), PCI Express, eSATA or Ethernet. A compatible connector port 120 of the portable device 100 receives the opposite end of the cable 118. In a USB implementation, for example, the USB cable 118 and associated connections and ports may support one or more of a USB version 1.1, 2.0, or 3.0 data transfer speeds. With such combined power and data connections, data may be exchanged between the portable medical infusion device 100 and a connected computer over the cable 118, and the portable medical device 100 may receive electrical power from the computer, as well.

Referring now to FIG. 2, a block diagram of the components within the portable medical device 100 of FIG. 1 is shown. The portable medical device 100 of this embodiment includes the housing 108 and includes a connector interface 20 coupled to the connector port 12 that receives a combined data/power cable, such as a standard, micro- or mini-USB cable 118 (illustrated in FIG. 1). The connector interface 20 supports data exchange and receives electrical power through the connector port 120 (illustrated in FIG. 1), and controls a connector data element 21a and a connector power element 21b. The connector interface 20 passes data communications from the connector port 11 through the connector data element 21a to a system bus 22, such as current updates to the programming of the portable medical device and/or current reminders saved such as, for example, on a computer program associated with the device 100. The connector interface 20 also passes electrical power from the connector port 12 through the connector power element 21b to a battery charger 29, which is coupled to a battery 28 and which recharges the battery capable of supporting operation of the portable medical device 100.

A control processor 23 is connected to the system bus 22 and receives the data communications from the connector data element 20 for processing. The control processor 23 controls operation of the various elements of the portable device 100 that are connected to the system bus 22. The control processor operates according to program instructions that may be stored in the device memory 24. Program instructions may also be stored in processor memory of the control processor 23. The control processor also stores data from its operations in the memory 24. The control processor controls a data communications element 25 that may comprise a receiver/transmitter for wireless RF communications, such as "WiFi" communications or "Bluetooth" communications between the portable medical device 10 and compatible external systems and networks. The portable infusion device may include an interface that allows a user such as a patient to interact with the programming of the processor to determine an amount of fluid to be delivered, a rate of delivery, a delivery profile, and/or the like.

As shown in FIG. 2, the portable medical device may include a processor, such as a control processor. The processor functions for controlling the overall functions of the portable infusion device. Specifically, the processor includes programming that functions to control the device and its components. The programming may comprise computer instructions stored in memory or firmware components that, when executed by the processor, provide the processing and features described herein. For instance, the processor may communicate with, e.g., send signals to and/or receives signals from, and/or otherwise control one or more of the delivery mechanism, reservoir, estimators, output mechanisms (e.g., display), memory, transmitter, receiver, alarm (s), speaker and clock or other features. The programming that is executed by the processor may be referred to herein as the "program" or "programming" of the device.

Accordingly, the processor may include programming that it can execute to control the speed of translation of a pump mechanism, the release of fluid from the reservoir, the data to be displayed by a display, the data to be transmitted via the transmitter, the one or more alarms, etc. The processor may also include programming that allows the processor to receive signals and/or other data from an input device, receiver, various sensors (such as a sensor that may be included as a part of the device or used in conjunction therewith, for instance, a blood glucose monitor and/or a blood glucose sensor, and the like) and to store the same in a memory. The memory can be any type of memory capable of storing data and communicating that data to one or more other components of the device, such as the processor.

The memory 24 of the device 100 may be any type of memory capable of storing data and retrieving that data for transfer to one or more other components of the device, such as the control processor 23. The memory 24 may comprise one or more of a flash memory, SRAM, ROM, DRAM, RAM, EPROM, dynamic storage, and the like. For the illustrated portable medical device 100 embodiment of FIG. 1, the memory 24 may be coupled to the control processor 23 and may be configured to receive and store input data and/or store one or more template or predetermined fluid delivery patterns. For example, the memory 24 can be configured to store one or more personalized (e.g., user defined) delivery profiles, such as a profile based on a user's selection and/or grouping of various input factors; past generated delivery profiles; recommended delivery profiles; one or more traditional delivery profiles, e.g., square wave, dual square wave, basal and bolus rate profiles; and/or the like. In certain embodiments, the portable infusion device is configured for receiving user information about a user's present or predicted conditions. Such information may include the amount of insulin already present in the body, (e.g., "insulin on board"); blood glucose level; trending blood glucose level; insulin sensitivity/insensitivity; glycemic index; information about the user's metabolism (e.g., "metabolic rate"); stress level; physiological conditions, (e.g., age, health, sickness, diurnal cycles, etc.); other measurable parameters (e.g., information related to amount/type of other hormones such as steroids, etc.); pharmacokinetics of the medicament (e.g., age of insulin, decay rate, etc.); information about the type and quantity of food to be or already ingested (e.g., carbohydrates, proteins, fat; activity; use history; calendared events); environment (e.g., temperature, humidity, pressure, etc.); and the like. One or more of these factors may be entered into the device, for instance, by an input device. In some embodiments, the memory 24 of the portable infusion device 10 may have a data capacity of up to or over about 10 GB, more specifically, up to about 3 GB, even more specifically, about 1 MB to about 200 MB. In some embodiments, the memory 24 of the device 10 may be up to about 3 GB, more specifically, up to about 500 MB, and even more specifically, about 200 kB to about 200 MB. The processor includes programming configured for receiving such user input information, such as that discussed above, parsing and collating the information to generate an output, and presenting that output to a user, such as on display. The device 100 includes an output/display component 26 such as the touchscreen 110 illustrated in FIG. 1, for operating virtual buttons or switches and the like, which may appear on the touchscreen.

The device 100 can comprise an insulin pump device, which therefore also includes a drive/pump element 27 such as a pumping mechanism for delivery of insulin fluid to the connecting tube 14, as described above in connection with FIG. 1. The delivery mechanism may be any suitable type of mechanism including the pumping mechanism. For some embodiments, the delivery mechanism may include a typical drive mechanism, such as a drive mechanism that includes a drive screw coupled to a motor. In such an instance, the drive mechanism may be configured for being operably coupled to a reservoir, such as a syringe based reservoir, and the housing may be sized to include at least a portion of the drive mechanism and the reservoir. In some instances, the delivery mechanism may include a hydraulics mechanism, pneumatic mechanism, step motor, continuous motor, or the like.

The actuator or drive mechanism may be configured for actuating or otherwise effecting the translation of a pump piston or element such as a spool or shuttlecock. The actuator may be any mechanism that is capable of causing the translation of the spool. For instance, the actuator may include an electric coil, a ferrite member, a nitinol member, a lever arm, corresponding magnets or electric magnets or dipoles.

As indicated above, the egress may be configured so as to communicate with the spool translation chamber and/or spool and/or one or more openings therein. The egress may further be configured for opening and closing or otherwise regulating the amount of fluid that is allowed to pass there through. In this manner, the reservoir interacts with the delivery mechanism to effectuate the delivery of a stored fluid from the reservoir, through the delivery mechanism, and out of the portable infusion device, e.g., via an infusion set.

Figure 3A:
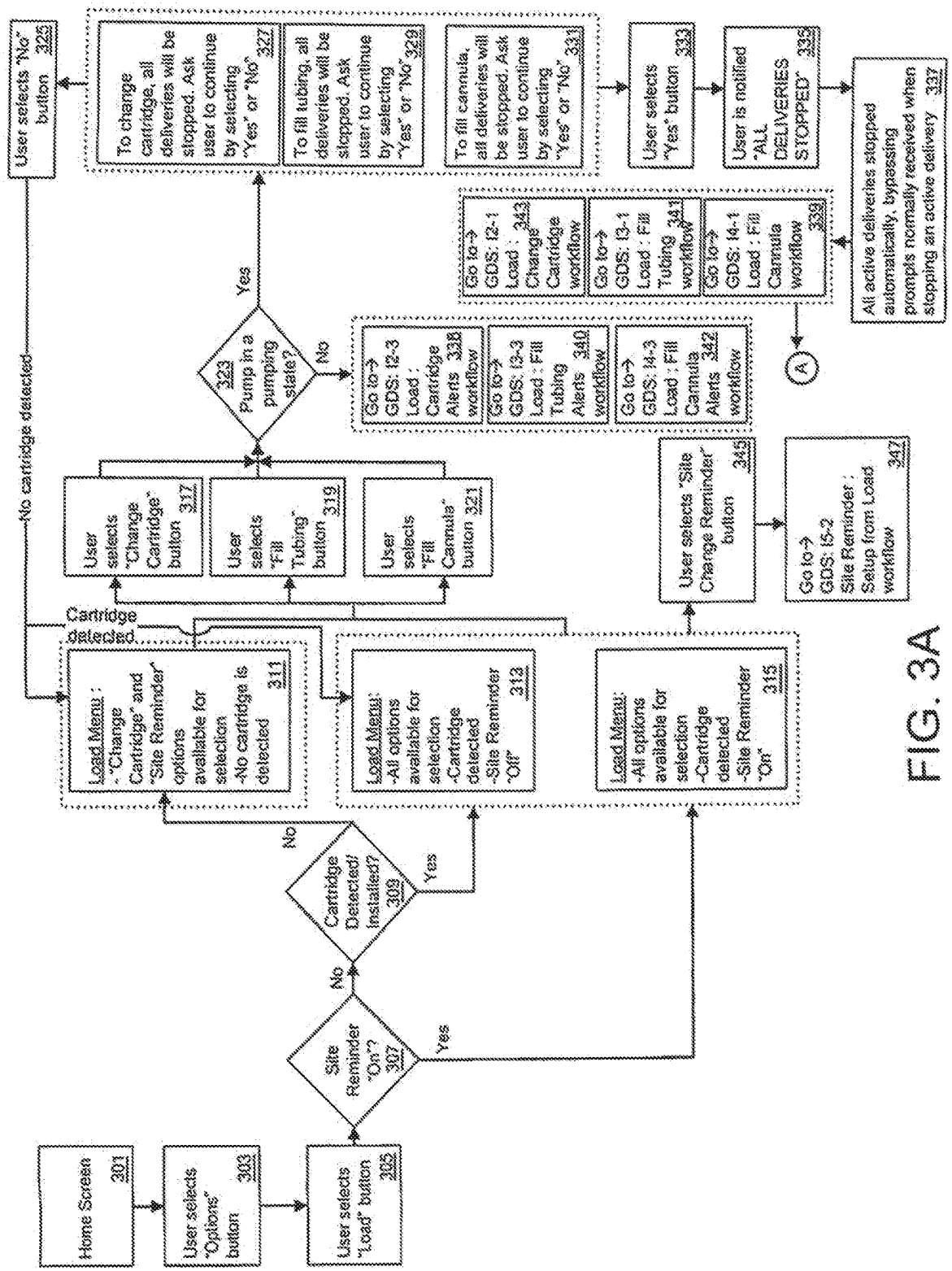
FIGS. 3A-3C are state diagrams that illustrate an exemplary load set-up sequence according to an embodiment of the present invention.
Figure 3B:
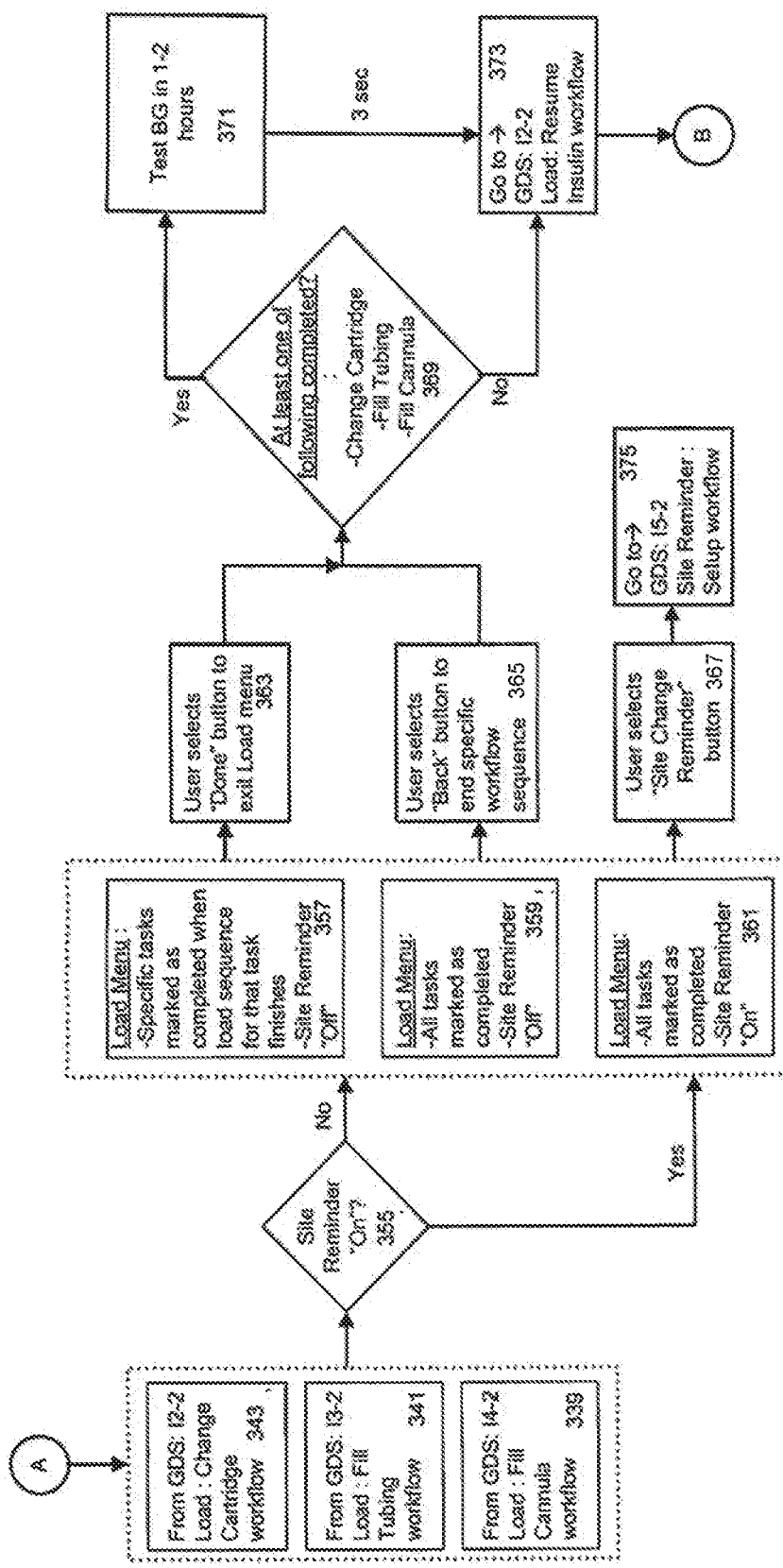
Figure 3C:
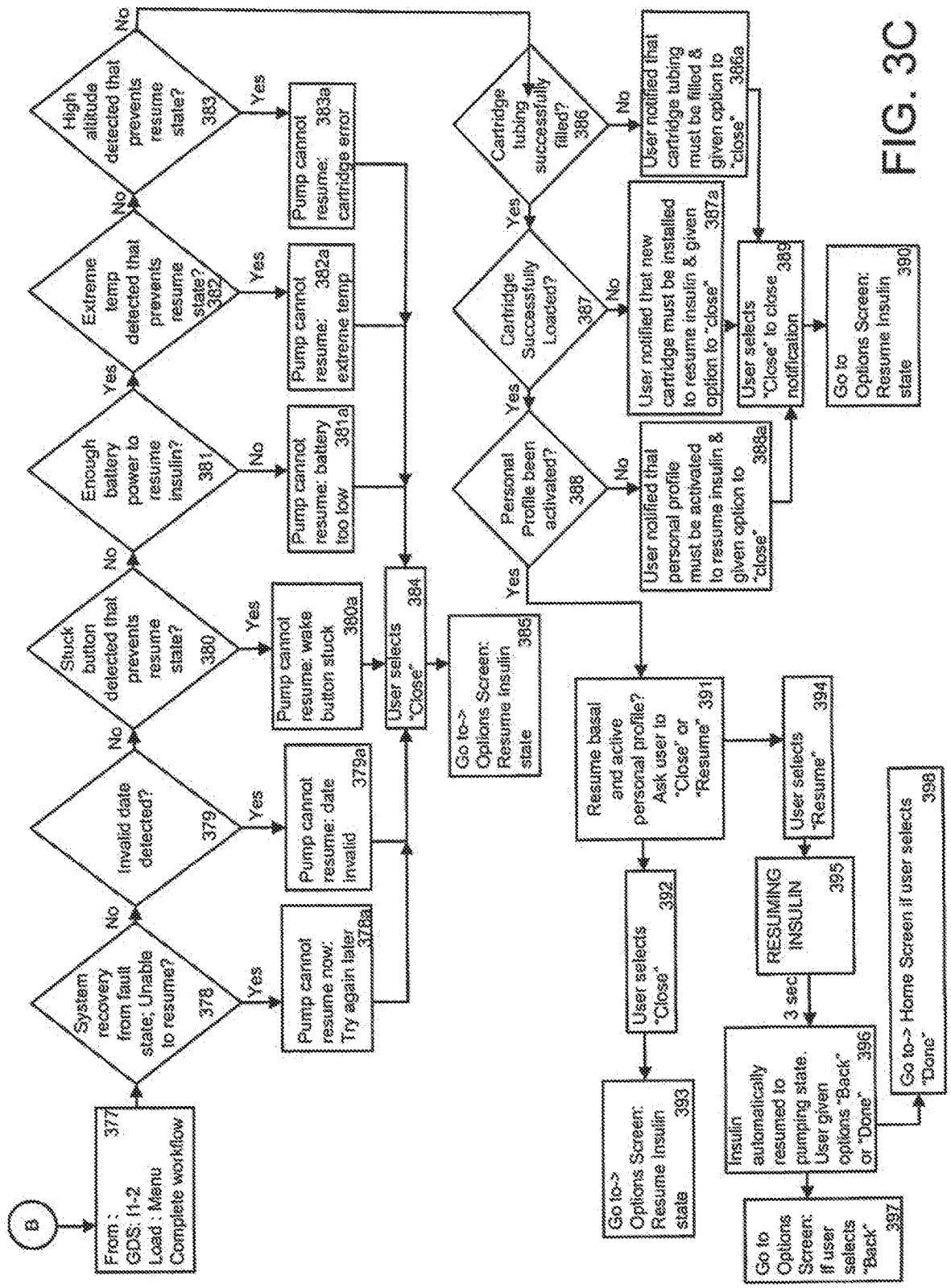

Referring now to FIGS. 3A-C, an exemplary sequence utilized to program a user defined profile into the memory element of the portable medical device is illustrated. As described in the following paragraphs, the programming and modification of current profiles within the portable medical device can be accomplished through user interactions with the touch screen, or display element, of the device. Each user interaction, e.g., touch, can be interpreted as an input to control and or navigate through screens of the device, dependent on the region of the display receiving the interaction. In further embodiments, modifications and programming of the user profiles can be completed on a computing device and downloaded to the portable medical device, once the device is coupled to the computing device. In other embodiments, the display screen of the portable medical device can further be utilized to provide confirmation that the user wishes to download and/or allow data communications with a particular computing device, e.g., 15 such as when a user utilizes a computing device solely to charge the portable medical device.

The user defined profile can allow the user to set alerts (e.g., site reminders), delivery amounts, temperature delivery rates, test times, and the like. The user-defined profile can also allow the user to change the physical state of the device, such as when a cartridge requires replacement, or when a tubing or cannula require filling. Modifying the physical state of the device, also affects the active physical state of the portable medical device, as described in the load sequence of FIGS. 3A-3C.

Figure 4:
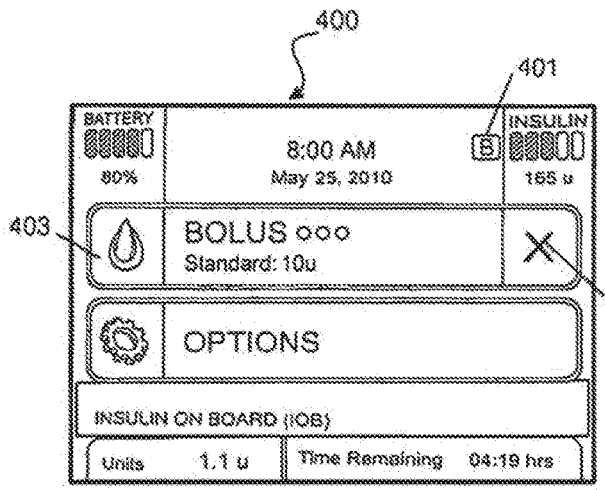
FIG. 4 is an exemplary screenshot of a home screen provided in FIG. 3A.

As shown in FIG. 3A, the user can initially be provided with a home screen 301, displayed on the touchscreen 110 (illustrated in FIG. 1). The home screen 301 allows the user to view various current conditions and states of the device. For example, FIG. 4 illustrates a home screen 400 that provides the conditions (clockwise from top left) of an 80% battery life remaining, the time (8:00 AM), the date (May 25, 2010), the insulin available in the cartridge (165u), the time remaining before the next scheduled injection (4:19 hours), the insulin on board (IOB) in units (1.1 u), an options button and a bolus button. The bolus button shows whether or not the bolus is in use, e.g., if the button is highlighted, and the current amount of bolus being administered. The bolus can be scheduled to be delivered at certain times of the day, e.g., mealtimes, such that the bolus button and insulin amounts automatically appear during those times. The current state 401 of the portable medical device is indicated by a letter ("B"), which appears proximate to the current cartridge amount (165u). As shown in FIG. 4, the current state of the device is "B", which is an active physical state, e.g., fluid is actively being pumped, having both basal delivery and bolus delivery. Other states not shown can include a red "T", which indicates an active physical state that provides a temperature rate delivery 0u/hr (zero units per hour); a red "0", which indicates a basal delivery rate at 0u/hr; "B", which is an active physical state having only basal delivery (if bolus delivery is not indicated on bolus button); and an orange "T", which indicates an active physical state that provides an active temperature rate delivery as programmed by the user.

As shown in FIG. 4, a bolus delivery state is indicated by the "X" 402 mark on a bolus button 403, and the amount of the bolus delivery is indicated as "Standard: 10 u" also on the bolus button 403. A standard bolus delivery state is indicated in FIG. 4. If the bolus is in an extended delivery state, the bolus button 403 can indicate "Extended: 10 u" along with the time of the extended delivery state, e.g., 8:00 AM-10:30 AM. The bolus can also be in a correction state, "Correction: 1 u" or a standard state with a correction "Standard/Correction: 10 u". As previously mentioned, if an "X" mark 402 does not appear on the bolus button, bolus delivery is off.

If no letter "B" 401 appears on the home screen, then the portable medical device is in an inactive state, and no basal or bolus deliveries are occurring. Such a state is shown in FIG. and will be described further with reference to FIGS. 3A-3B in the following paragraphs. The inactive state can be noted on the home screen on the Options button as "All Deliveries Stopped". It should be noted that if the basal delivery is "off", e.g., an inactive physical state, the bolus delivery state is automatically shown as being in an "off" state as well.

Referring to FIG. 3A, the user can navigate to the options menu by selecting the "Options" button on the home screen as shown in step 303. The user can then be provided with several options, including the option to "Load", which modifies the physical state of the device. Once the user selects the Load option, in step 305, the processor of the portable medical device performs a check to determine the state of the Site Reminder, e.g., "On" or "Off" in step 307. If the Site Reminder is not "On", the device setup is considered to be in an incomplete state.

Figure 5:
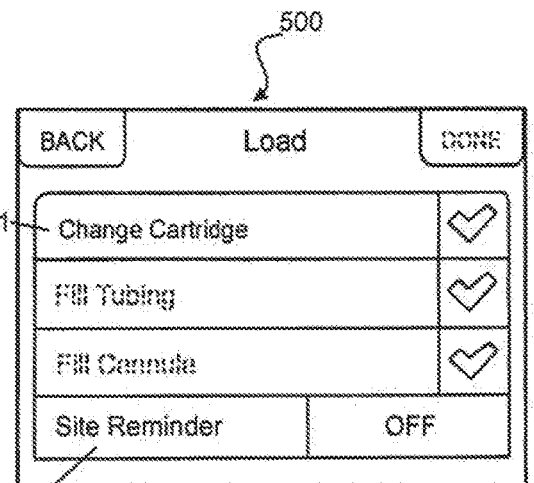
FIG. 5 is an exemplary screenshot of a load screen having two available options for selection by the user provided in FIG. 3A.

In step 309, if the Site Reminder is "Off", the device then checks to determine if a cartridge is installed/detected within the device. If a cartridge is not detected, the portable medical device provides the user with only two options in the load menu 311: 1) enter the change cartridge load sequence, or 2) enter the site reminder edit sequence (to turn on and program the Site Reminder function). FIG. 5 illustrates an exemplary screenshot 500 of a device that does not detect a cartridge and that has the Site Reminder turned off. As shown in FIG. 5, only the Site Reminder button 502 and the Change Cartridge button are available for selection by the user in the load menu. The user then can then select to change the cartridge, e.g., load a cartridge into the device and/or correct an erroneously loaded/detected cartridge in the device as shown in step 317. The change cartridge load sequence is described in following paragraphs.

Referring to FIG. 3A, in step 309, if a cartridge is detected when the state of the Site Reminder is "Off", the user is directed to a load menu 313, which includes all load functions available for selection, and reminds the user that the Site Reminder is "Off". Accordingly, from load menu 313, the user can begin any load sequence option and/or change the state of the Site Reminder. The Site Reminder is an independent setting, and can be edited without completing any of the flows (e.g., Change Cartridge, Fill Tubing or Fill Cannula) and/or during a pumping or non-pumping state. However, in one embodiment, when the Site Reminder is set to an "On" position, it can be part of the Fill Cannula sequence in order to help encourage the user to set it up.

Referring to step 307, if the site reminder is set to "On", the user is shown a load menu 315 in which all load sequence options are available for selection by the user and the Site Reminder button indicates an "On" state. From the load menu 315, the user can select any option previously described along with the option to change the Site Reminder. If the user selects to change the Site Reminder as shown in step 345, the device then enters a workflow sequence "15-2", show in box 347, to setup the site reminder from the load workflow. The set up of the Site Reminder from the load menu is slightly different than from the Fill Cannula workflow sequence. If the Site Reminder is set up through the load menu 315 as shown in step 345, the user is able to press a "Back" button to return to the load menu 315 at any time. However, if the user modifies the Site Reminder from the Fill Cannula workflow sequence, the "Back" button is inactive as the user cannot return to a previous state in the Fill Cannula workflow sequence until the sequence is completed. Accordingly, the Site Reminder is editable through the load menu and/or through the Fill Cannula sequence, though slight variations occur within the sequence which is followed for each setup.

Figure 6:
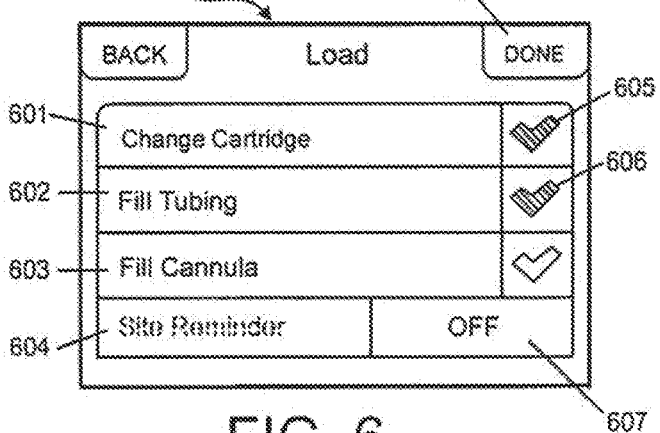
FIG. 6 is an exemplary screenshot of a load screen having all available options for selection by the user provided in FIG. 3B.

Referring to load menus shown in boxes 311 (sequence 317 only), 313, and 315, the user can select a button to enter a load sequence, such as one of the buttons comprising Change Cartridge 317, Fill Tubing 319, or Fill Cannula 321. Each of the load sequence options is illustrated in FIG. 6. As each load sequence is completed, the button, which the user can select for each particular sequence, indicates a completed mark (check mark) 605, 606. As shown in an exemplary screenshot 600 of FIG. 6, the Change Cartridge 601 load sequence and the Fill Tubing 602 load sequence have each been completed. The Fill Cannula 603 has not been completed, but is available for selection because a cartridge is detected in the device.

Furthermore, the Site Reminder 604 option is available for set-up due to its current "Off" state 607. Once at least one load sequence option has been selected and completed, the user can be provided with the option to complete the session in the menu by selecting the "Done" button 608 on the interactive touchscreen.

In step 323, if the user selects any one of the aforementioned load sequences, the processor of the device checks the pumping mechanism in order to determine if it is in an active pumping state. If the pump is not in an active state when a load sequence is selected, the user is sent to a corresponding workflow alert state. For example, if the user chose to load a cartridge, and the device is not in an active pumping state, the user is sent to a change cartridge alerts workflow, as shown in box 338. Similarly, if the device is in an inactive state and the user chose to enter a fill tubing workflow or a fill cannula workflow, the user is directed to each respective workflow as shown in boxes 340 and 342, respectively. If the pump is in an active state, the active physical state of the portable medical device should be stopped. Accordingly, the user is directed to a screen, which requires a user input to confirm that the active operation; e.g., pumping, of the portable medical device will be stopped. The user is then asked to enter "Yes" or "No" inputs for each of the load sequences to begin as shown in boxes 327, 329 and 331. This is provided in order for the user to avoid unwanted stopping of the pump, such as when a current scheduled infusion is occurring.

Figure 7:
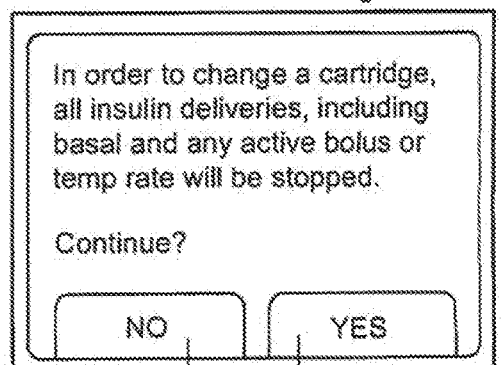
FIG. 7 is an exemplary screenshot of a confirmation screen for selection of a state change provided in FIGS. 3A-3B.

FIG. 7 shows an exemplary screenshot of the confirmation screen 700 on the display of the device for stopping the active operation. In the particular screen 700 shown, the display notifies the user that a selection of the Change Cartridge load sequence will cause all deliveries to be stopped. The user is given two options 701, in the form of two alternative touchscreen buttons, either to continue the Change Cartridge load sequence with "Yes" or to exit the load sequence request with the "No" button. If the user selects the "No" button, the device returns back to the same load menu previously displayed. As shown in FIG. 3A, the selection of the "No" button is illustrated in step 325 and returns the user to a load menu 311, 313, or 315. Alternatively, if the user selects the "Yes" button to confirm entering the load sequence, as in step 333, the user is provided with a final confirmation screen. The final confirmation screen can be an alert to the user that provides the user with a notification that the current active physical state of the device has changed; e.g., all deliveries have been stopped, a provided in step 335. The final confirmation screen can remain on the screen of the device until the next step in the load sequence is complete, such as the replacement of a cartridge, or until the user has acknowledged the physical state change of the device for a second time; e.g., the first time being screen 700 with option 701 in FIG. 7.

Figure 8:
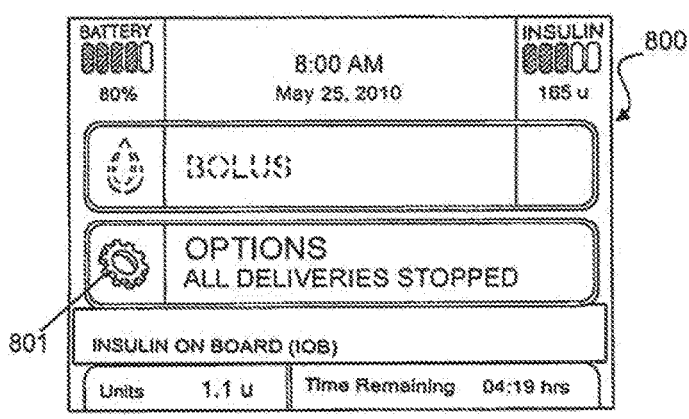
FIG. 8 is an exemplary screenshot of a home screen showing a delivery stop state provided in FIGS. 3A-3B.

Referring to FIG. 8, when the device enters the Change Cartridge load sequence, or another load sequence in which the physical state of the device has changed, notification or alert reflecting the current state of the device is also displayed on the main menu screen 800 of the device. Accordingly, the Bolus delivery button is unavailable and the options button 801 indicates that "All Deliveries Stopped" at the current time. In an embodiment where the device is in a Change Cartridge load sequence, the device then automatically stops all deliveries and bypasses prompts received when stopping individual delivery types (e.g., bolus, basal, temperature), as shown in state 335. Dependent on the load sequence chosen in boxes 317, 319. 321, the processor can direct the device to enter the particular load sequence 343, 341, 339.

Referring now to FIG. 3B, after completing one or more of the load sequences 343, 341, 339 selected by the user in FIG. 3A, the processor of the device then determines whether the Site Reminder is in an "On" or "Off" state. If the Site Reminder is in the "Off" state, then the user can be directed to a Load Menu that indicates one or more of the load sequences have been completed, such as shown in the exemplary screenshot of FIG. 6. For example, box 357 can show the user that specific tasks such as the "Change Cartridge" load sequence has been completed and/or the "Fill Cannula" load sequence has been completed. Each completed load sequence can have an illuminated, or highlighted, checkmark on that load option button.

If the Site Reminder is in the "On" state, then as shown in box 359, when all load sequences have been requested and completed by the user, the user can still be directed to the Load menu in order to configure and/or change the Site Reminder to the "On" state, since the portable medical device is then prepared for an active physical state. If the user has completed all load sequences and the Site Reminder is in the "On" state, the user can be provided with an option to enter an input of "Done" for the current workflow session. In some embodiments, if all load sequences, in particular the Fill Cannula load sequence, is complete, the Fill Cannula button is not active, or highlighted, for selection by the user though the completed checkmark is visible (e.g., highlighted or lit). This prevents the user from requesting an overflow of the cannula.

Referring again to boxes 357 and 359, once the user has entered and completed a particular load sequence, the user can be provided with, e.g., three (3) options to navigate away from the current device state. For example, in order for the user to exit the Load Menu and end a current workflow session, the user can select the "Done" button on the touchscreen of the device as provided in box 363. The Done button can take the user back to the Home Screen of the device, such as shown in FIG. 4. However, as previously mentioned, the Done button is only available for selection if at least one of the load sequences has been completed after selection by the user, as shown in the device check state of 369. If the portable medical device has completed at least one load sequence, the user is shown a screen indicating that the user should perform "Test BG in 1-2 hours" (blood glucose) as provided in box 371. This should be performed in order for the user to determine if all device components and physical modifications; e.g., cartridge change, cannula fill, tubing fill, were completed successfully. The user does not need to navigate away from the screen described in box 371, because the device can automatically navigate to a sequence to start an active state of resuming insulin workflow as provided in box 373. In an alternative embodiment, if no load sequence is determined as being completed by the device in the check state of 369, the device can automatically navigate to the resume active state in box 3 73. This may occur when the user has entered the load menu to view each available load option and/or edit the Site Reminder settings and/or has exited a load sequence prior to completion and is exciting the current load session Load menu.

Referring to the Load menus 357, 359, 361, in a second option to navigate away from any of these screens, the user can select the "Back" button. The Back button takes the user out of the current workflow session, or a specific workflow sequence in which the device currently is, to the Options menu. Prior to displaying the Options menu to the user, the system can run a similar check state of 369 discussed in the previous paragraph, which navigates to the notification screen of "Test BG in 1-2 hours" in box 3 71 if at least one load sequence has been completed and then to the resume active state 3 73. Again, the device bypasses the notification in box 3 71 if no load sequence has been completed by the device, and automatically enters the resume active state workflow in box 3 73. Once in the active state and not in the locked state, such as when the device is capable of being unlocked, the user is free to navigate through the device to perform tasks such as selecting custom options, editing and generating profiles, and viewing stored data.

Referring now to FIG. 3C, though the user can navigate away from the Load menu with the Back button or Done button as provided in FIG. 3B, the device performs a series of checks prior to allowing the device to resume an active state in a Menu Complete workflow sequence as shown in box 377 of FIG. 3C. In some cases, the user is notified with an error message and in others the user is asked to confirm that the active state will be resumed. In some embodiments, the only way for the portable medical device to commence an active state is for certain conditions associated with the Load menu to be satisfied. The conditions are further explained in the following paragraphs with references to corresponding exemplary screenshots in FIGS. 9-11.

As shown in FIG. 3C, once the Menu Complete workflow sequence has begun, the device first checks if the device is recovering from a fault state in state 378, such as a mechanical or software failure state. If the device is recovering from a fault state, the user can receive an error message indicating that the portable medical device cannot enter an active state; e.g., the pump cannot resume pumping as shown in box 3 78a. The user is then asked to confirm that the error message has been read in box 378a, by selecting a "Close" button provided in box 384. This ensures that the user is aware of the fact that no insulin will be received from the device and other injection methods may be required. The user is then directed to an Options menu for "Resume Insulin state" provided in box 385 in order to troubleshoot the current detected error. All active operation of the device, e.g., pumping, remains in the "Off" state and no deliveries are occurring.

If the device is not recovering from a fault state, the processor then runs a second check to determine if the date provided on the device is valid, as provided in state 3 79. If the check fails; e.g., the date is incorrect, the user can receive an error message indicating the problem in box 379a. The user is then asked to confirm receipt of the error message by selecting a "Close" button as provided in box 384. The user is then directed to the Options menu for "Resume Insulin state" provided in box 385 in order to troubleshoot the current detected error. All active operation of the device; e.g., pumping, remains in the "Off" state and no deliveries are occurring.

If the device has a valid date, the processor then runs a third check to determine if the mechanical components, such as the buttons on the touchscreen or other push buttons on the device, are malfunctioning as provided in state 380. If a button is malfunctioning, such as by being stuck, the user is again notified via an error message in 380a that the device will not resume an active pumping state. The user is then asked to confirm receipt of the error message by selecting a "Close" button as provided in state 384. The user is then directed to the Options menu for "Resume Insulin state" provided in box 385 in order to troubleshoot the current detected error. All active operation of the device; e.g., pumping, remains in the "Off" state and no deliveries are occurring.

Figure 9:
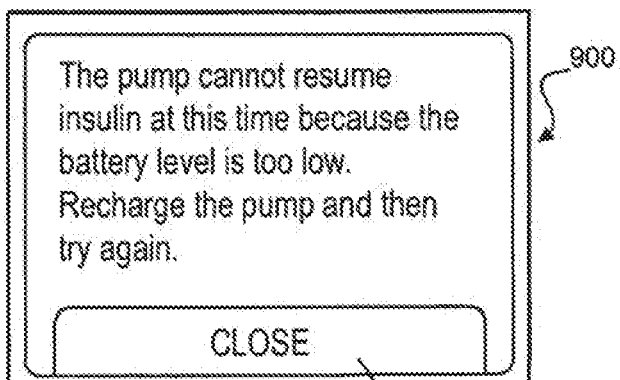
FIG. 9 is an exemplary screenshot of a notification screen in FIG. 3C.

Referring to FIG. 9, if the device passes the third check, and all buttons are fully functional, the processor checks the current battery level within the device as in state 381. This ensures proper delivery of the infusion fluid, e.g., insulin, will occur at the scheduled times determined by the stored user profile. If the battery level is too low, the processor provides the user with a notification 900 in the form of an error message indicating a low battery level in box 381a. The user is then asked to confirm receipt of the error message by selecting a "Close" button 901 as provided in box 384. The user is then directed to the Options menu for "Resume Insulin state" provided in box 385 in order to troubleshoot the current detected error. All active operation of the device; e.g., pumping, remains in the "Off" state and no deliveries are allowed to occur.

If the portable medical device has sufficient battery power to operate in an active state, the processor performs the next check to determine if any outside factors may affect the correct operation of the device. As shown in state 382, the fourth check is utilized to determine if the processor detects any extreme temperatures. Extreme temperatures may be the result of outside conditions, such as extremely hot or cold outside temperatures. In the case of an extremely hot temperature, the user is again provided with an error message indicating that the device detects a high temperature provided in box 382a, and the user is then asked to confirm receipt of the error message by selecting a "Close" button as provided in box 384. The user is then directed to the Options menu for "Resume Insulin state" provided in box 385 in order to troubleshoot the current detected error. All active operation of the device, e.g., pumping, remains in the "Off" state and no medicament delivery is occurring. In some embodiments, a similar operation is provided in the case of an extremely cold temperature.

Finally, the processor of the portable medical device performs a fifth check to again determine if an additional outside factor of altitude is detected in state 383. If an abnormal altitude is detected, the device may not operate properly. Accordingly, if a high altitude is detected, then the user is provided a notification of high altitude being detected such that an active state cannot be resumed in box 383a. The user is then asked to confirm receipt of the error message by selecting a "Close" button as provided in box 384.

If the processor of the device detects a suitable altitude for operation, the Load Menu Complete workflow sequence then performs individual checks of the physical components of the device that provide proper active operation in states 386, 387 and 388. The processor of the portable medical device first determines if the Cartridge Tubing has been filled in state 386. If the tubing is not filled, the user is provided a sequence of screens similar to the aforementioned checks. First, the user is notified in an error message in box 386a that the Cartridge Tubing must be filled to continue with active operation of the portable medical device. The user is then asked to confirm receipt of the error message by selecting a "Close" button as provided in box 389. The user is then directed to the Options menu for "Resume Insulin state" provided in box 390 in order to troubleshoot the current detected error. All active operation of the device, e.g., pumping, remains in the "Off" state and no deliveries are occurring.

Next, if the cartridge tubing is successfully filled as noted by the green check mark on the "Fill Tubing" bar 602, the processor of the device performs a check to determine if the cartridge has been successfully loaded into the device in state 387a. If the cartridge was installed incorrectly, the user is notified in an error message that the cartridge requires reinstallation. The user is then asked to confirm receipt of the error message by selecting a "Close" button as provided in box 389. The user is then directed to the Options menu for "Resume Insulin state" provided in box 390 in order to troubleshoot the current detected error. All active operation of the device; e.g., pumping, remains in the "Off" state and no deliveries are occurring.

Figure 10:
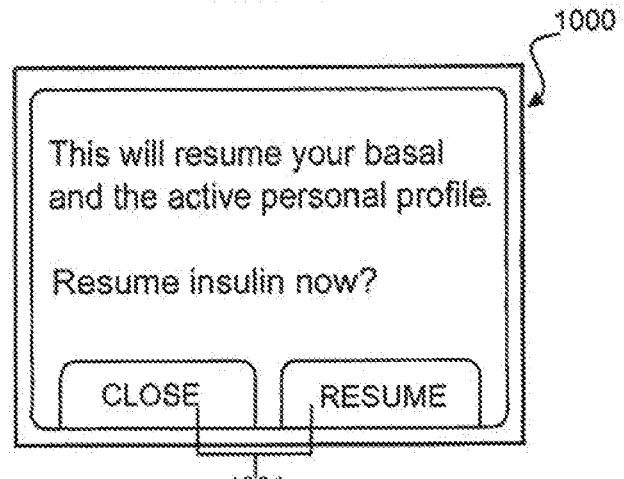
FIG. 10 is an exemplary screenshot of a state change confirmation screen in FIG. 3C.

Referring to FIG. 10, once the device processor runs through all checks on the device and the device determines that all components are functional, the user is then directed to an Options screen to "Resume Insulin Now" 1000. This is presented when the device is in a functional operating state and the user programmed profiles and deliveries can be safely resumed. The user is provided with two options 1001 to "Resume" or "Close" the Options screen; e.g., if the user wishes to perform another load sequence.

Figure 11:
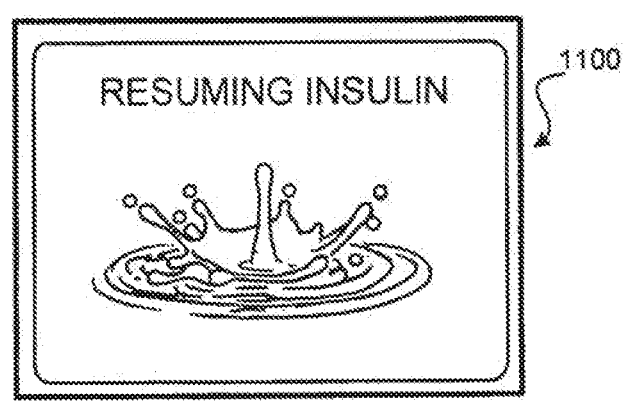
FIG. 11 is an exemplary screenshot of a current state notification screen in FIG. 3C.

Referring to FIG. 11, if the user selects to "Resume" the active state of the device, the device can indicate to the user that the device is "Resuming Insulin" deliveries as shown in screenshot 1100. In some embodiments, the "Resuming Insulin" screen 1100 can remain on the device until a first insulin delivery has been made. In other embodiments, the "Resuming Insulin" screen 1100 can remain on the screen of the device for a predetermined time period, such as 10 seconds.

In the previously described Load Menu Complete workflow sequence, it should be understood that all or some of the checks performed on the device can be sequentially or simultaneously performed. Additionally, at any step within the Load Menu Complete workflow sequence, similar to any step navigating through the device from the Home screen to the Option Menu and, subsequently, to the Load Menu, the user is provided with at least two options to navigate away from current screen by selecting a "Yes", "No", "Continue", "Back" or "Close" button. The "Close" button allows the device to remain in a hold state in order for a notification message to be confirmed by the user. However, after acceptance, e.g., interaction with the screen on the "Close" button, the user is directed to a following screen which offers two or more options for the user to navigate through functions of the device; e.g., the load sequence options on the Load menu.

Figure 12A:
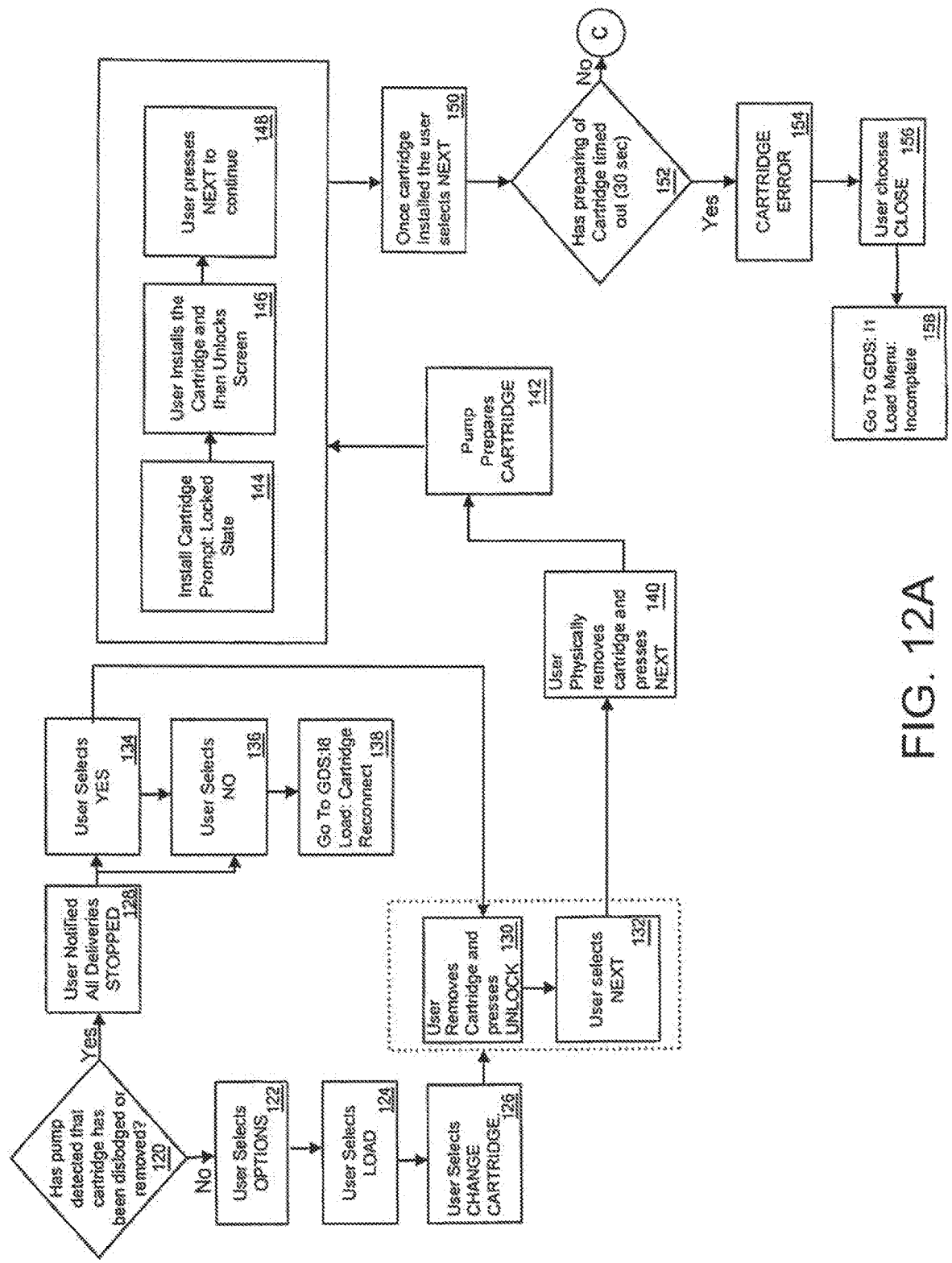
FIGS. 12A-12B are state diagrams that illustrate an exemplary change cartridge sequence in an embodiment of the present invention.
Figure 12B:
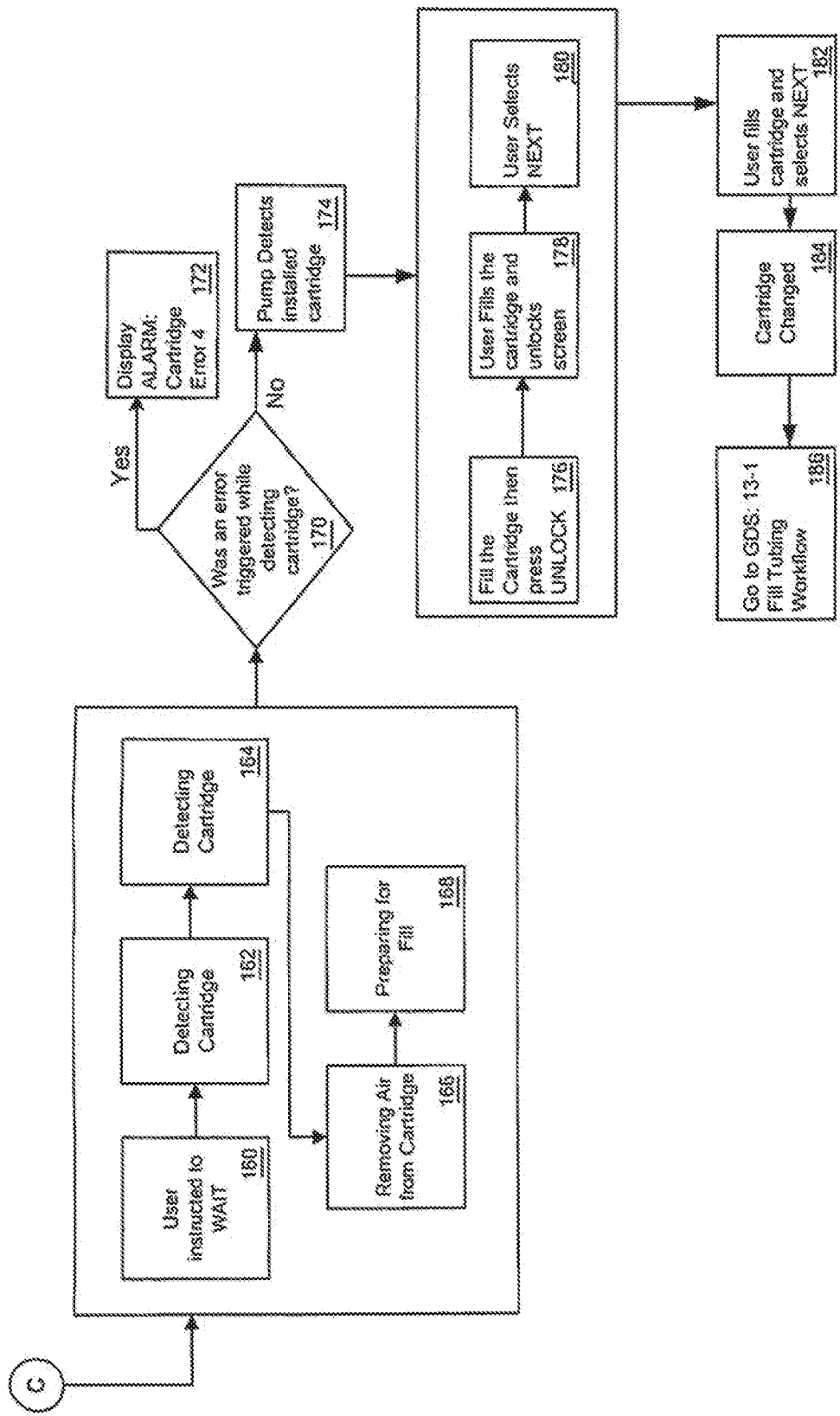

Referring now to FIGS. 12A-12B, a load sequence workflow for changing a cartridge on the device is described with further reference to FIGS. 13-16.

Figure 13:
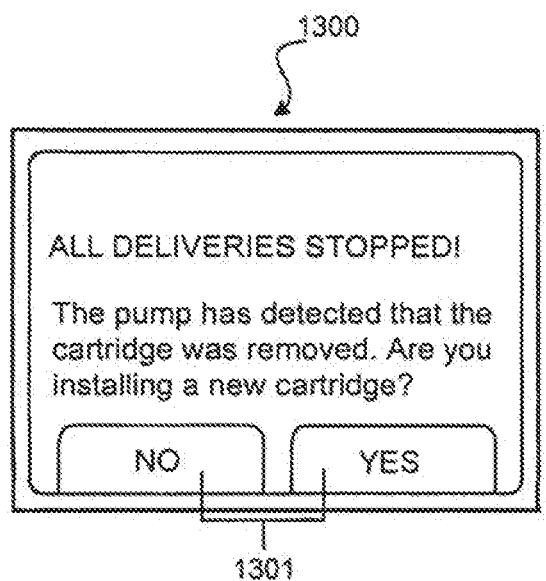
FIG. 13 is an exemplary screenshot of a alert screen provided in the sequence of FIG. 12A.
Figure 14:
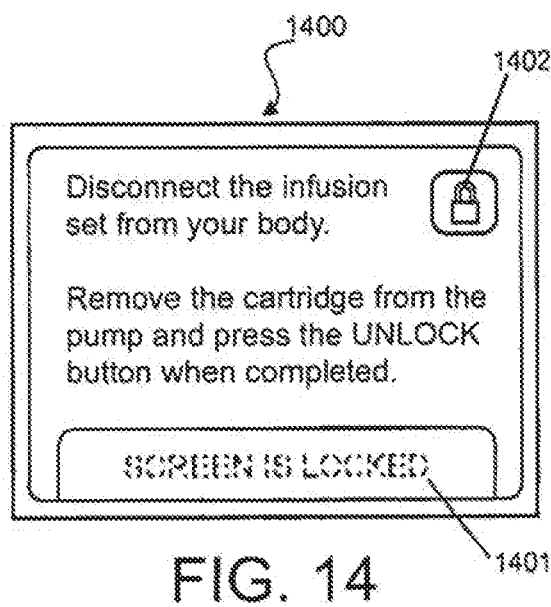
FIG. 14 is an exemplary screenshot of a notification screen provided in the sequence of FIG. 12A.

As shown in FIG. 12A, the change cartridge load sequence, which can be initialized through the Load menu described in FIGS. 3A-3C, begins with a device check process in state 120 to determine if a cartridge is currently installed and/or installed correctly in the device. If no cartridge and/or a erroneously installed cartridge is detected by the processor, the user is directed to an notification screen including an alert that indicates an error with the cartridge provided in box 128. An exemplary screenshot of box 128 is shown in FIG. 13. As previously discussed, once the user enters the load sequence for changing a cartridge, either inadvertently (e.g., incorrect removal/installation of cartridge at box 128) or intentionally (e.g., navigation through load menu at box 126), all deliveries and active operation of the device are stopped.

Referring again to FIG. 12A, if the user is shown the notification in state 128, two options are provided to navigate away from the notification screen, "Yes" and "No". These two options 1301 are also shown in the exemplary notification, or alert screenshot 1300 of FIG. 13. If the user selects "No" shown in box 136, the processor of the device directs the user to begin a load sequence for reconnecting the incorrectly installed cartridge of the device as shown in box 138. If the user selects that a cartridge is currently being installed, "Yes" in box 134, the user can then be directed by the processor to the predefined Change Cartridge load sequence screens. The screens are provided in order to guide the user through the cartridge changing process with simple instructions and failsafe mechanisms to ensure that proper device functions occur.

In particular, the Change Cartridge load sequence, along with the Fill Tubing and Fill Cannula load sequences, includes a failsafe mechanism that locks the screen of the device during a physical modification (e.g., removal/installation of cartridge, filling of cannula, etc.) such that any inadvertent interaction with the screen of the device is avoided. Accordingly, though the device is still functional; e.g., background processing is occurring, the current state of the device cannot be modified until the screen is unlocked. For example, if the user touches the screen of the device while removing the cartridge or filling the tubing, the screen will not input the touch that causes the device 1301 to move away from the current screen in the workflow process and begin, for example, the delivery of the insulin to the tube when disconnected from the patient on accident.

As provided in FIG. 12A, when the device is instructed to enter the change cartridge load sequence in box 126 in response to a user input, the user is notified on the device screen when it is safe to remove the infusion from his/her body in box 130. The user is also instructed to the remove the cartridge from the device and is informed that the device screen is currently in a locked state. As shown in box 130, an additional icon appears on the user's device screen, indicating that the screen of the device is locked; e.g., a padlock icon. This icon and box 130 are provided in an exemplary screenshot 1400 in FIG. 14. The icon 1402 covers a small region of the display screen and, when active, indicates that any other surface of display screen is not capable of receiving an input, e.g., through a physical interaction with the device. The indication that the screen is in a locked state 1401 is also shown, but is not active, e.g., highlighted, as this region is not currently able to receive an input. Accordingly, in order to for the user to view the next screen in the cartridge change load sequence, the user is provided with only one option to provide a single (1) predefined input. The user can then touch the screen on the lock icon 1402 after which the user is directed to a second predefined screen that ensures the user has completed the task at hand and confirms that the user is prepared to move forward in the current load sequence.

Figure 15:
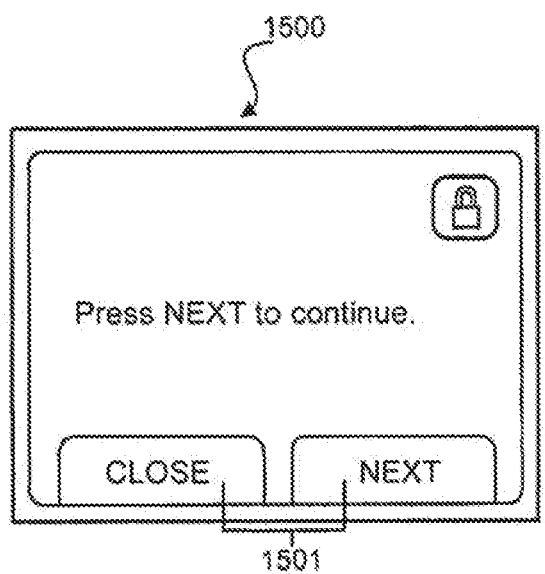
FIG. 15 is an exemplary screenshot of a state change confirmation screen provided in the sequence of FIG. 12A.

Referring again to FIG. 12A, when the user has selected to unlock the first locked screen state in box 130 (e.g., through selection of the lock button 1402 in FIG. 14), the user is provided with a subsequent screen to confirm that he/she would like to continue through the current load sequence, such as the Change Cartridge load sequence provided in box 132. It is important to note that the screen provided in the screen sequence immediately following the user's first request to unlock the screen of the device is the screen described in box 132. The user is unable to navigate from a first locked screen state that appears during a physical state change of the device to any other screen except the subsequent confirmation screen provided in box 132. An exemplary screen shot of box 132 is illustrated in FIG. 15. As shown in FIG. 15, the only two options the user has to navigate away from the screen is through selection of "Next" or "Close" to continue with the selected load sequence. If the user selects "Close", the load sequence is discontinued and the user is directed back to the Load Menu. At such a point in the sequence, the device should not include a cartridge and, thus, the user will be only provided the "Change Cartridge" and "Set Reminder" options in the Load Menu. The screen will no longer be in a locked state once it displays the Load Menu. Accordingly, the user will be able to navigate through device.

If the user enters "Next" in box 132 of FIG. 12A, the user is directed to a notification screen in the load sequence, indicating the operation in progress on the device. For example, as provided in box 142, the user is notified that the device is preparing for a cartridge to be installed. At this point, the screen is still in a locked state and no user input which may change the active state of the device is permitted. Only specified regions of the screen will accept an input from the user on screens which the device has predefined as input regions allowing that user to move in a particular load sequence and/or exit the load sequence to return to the Load Menu. For example, the screen described in box 142 does not include any input regions on the screen which may allow the user to navigate to another screen. Additionally, the screen is in a locked state. Accordingly, the device can receive no input until the specified operation completes within the device.

Referring still to FIG. 12A, once the device has completed preparing the cartridge, as described in box 142, the user is shown a screen indicating the next step in the load sequence which is to be performed. In box 144, the user is instructed to install a new cartridge in the portable device. In some embodiments, the user is provided with a visual graphic to facilitate such physical operation. In box 144, the user can also be notified and reminded that the screen is currently in a lock state, and no other state changes can occur in the device. Furthermore, the user can be provided with instruction to touch, or press, the unlock button to move forward through the selected load sequence. Again, similar to the sequence described previously, because a physical state change has just occurred on the device (e.g., a cartridge is installed), the user is directed to a confirmation screen which allows the user to continue through the load sequence or exit to the load menu in box 148.

Referring to FIG. 15, the user can again be requested to enter one of two options: "Close" or "Next" display buttons 1501, shown in the exemplary confirmation screenshot 1500 in FIG. 15. In some embodiments, the confirmation screen 1500 can also include a visual graphic for the user to see how the current physical state of the device should appear. If the user selects "Close" the device exits the current load sequence and returns to the Load Menu. At the Load menu, if the user selects "Next", the processor of the device executes a check to detect if the cartridge preparing time has exceeded a threshold value such as, for example, 30 seconds. If the cartridge was installed incorrectly or cannot be recognized by the device, the user is provided with an error message indicating that the cartridge installed cannot be utilized by the device and should be removed and replaced, as provided in box 154. The user is provided with one option to "Close" the current screen displaying the error message in box 156, as the load sequence cannot continue with a problematic cartridge. Once the user selects to close the screen in box 156, the user is then directed to the Load Menu in box 158.

Referring now to FIG. 12B, if the user correctly installed the cartridge in the load sequence described in FIG. 12A, and the processor of the device has recognized and prepared the cartridge for use, the user is shown a series of screens indicating the current operation in progress. For example, the user can be shown a series of screens which are utilized while the device completes certain steps of the load sequence operation such as "Please Wait", shown when the device begins the cartridge detection process, "Detecting Cartridge", shown when the device is detecting the cartridge, "Removing Air from Cartridge", shown when the device is removing air from the cartridge, and "Preparing for a Fill", shown when the device is ready for the next step in the load sequence.

Figure 16:
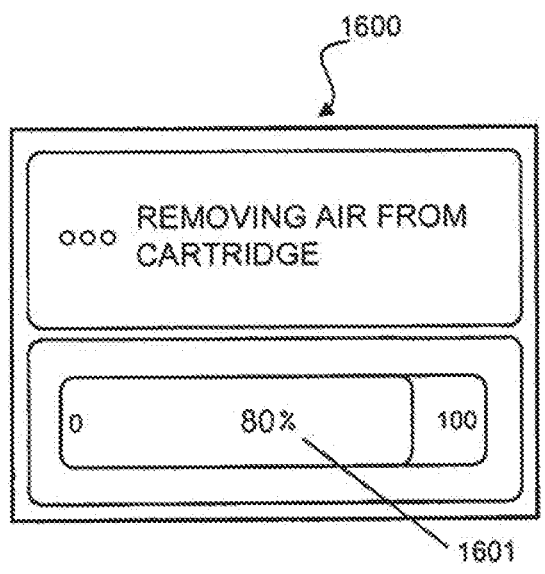
FIG. 16 is an exemplary screenshot of a notification screen provided in the sequence of FIG. 12B.

FIG. 16 provides an exemplary screenshot 1600 of the screens notifying the user of the current progress of the step in the load sequence. As shown, the user is notified that the device is currently operating to remove air from the cartridge, "Removing Air From Cartridge," and a progress bar 1601 indicates that the installation process is 80 percent (%) complete. The progress bar can be included in each of the aforementioned screens indicating the current progress of the operations being performed in the load sequence. It should be noted that though no "lock" icon is displayed on the screen during the operation in progress screen series just described, the screen is still in a locked state and no user inputs are capable of being received by the device.

Referring again to FIG. 12B, once the cartridge is installed and the detection and air removal processes have been performed by the processor to prepare the cartridge for use, the processor can execute a check to determine if any errors occurred during the cartridge detection process as shown in state 1 7 0. If an error occurred, the user can be shown an error message alerting the user that a cartridge error has occurred in box 172. If no errors occurred during installation and detection; e.g., the processor of the device detects the cartridge and the air is properly removed, the load sequence can continue to the next step. As provided in box 176, describing the next step in the change cartridge load sequence, the user is provided with the next set of instructions to fill the cartridge; e.g., with insulin, and then touch the "Unlock" (press the Lock icon) when done. The user can also be reminded of the current locked screen state, as depicted in a previous embodiment and shown in exemplary screenshot FIG. 14 in element 1401.

Once the user completes the load sequence step of filling the cartridge and selecting the "Unlock" button, the processor only allows the user to navigate to the next confirmation screen with selection of the unlock button after a physical state change has occurred on the device. The confirmation screen provided in box 180 is similar to those previously described in boxes 132 and 148 of FIG. 12A. The user is provided with two options to continue in the load sequence, "Close" or "Next". If the user selects "Close", the user is directed to the Load Menu. If the user selects "Next", the user is shown a notification message indicating the cartridge was successfully changed as provided in box 184. After the notification message is displayed for a predetermined amount of time sufficient for user viewing, the processor of the device directs the user to the next load sequence, such as, for example, the Fill Tubing workflow provided in box 186.

As previously described with reference to boxes 132 and 148 of FIG. 12A, and box 180 of FIG. 12B, if the user selects to "Close" the current workflow, or load sequence, the user is directed back to the Load Menu. Though transparent to the user, the processor determines that the current workflow is incomplete and runs a series of checks when such a selection is made in order to determine the current physical state of the device and to determine which operations need to occur in order for the device to function properly. Accordingly, each time the user selects to prematurely close out of the workflow sequence, the device runs through the checks, for example, previously described with reference to FIG. 3C.

In further embodiments, the user can enter the Fill Tubing workflow, or Load Sequence from the Load Menu. Further details of such operations will be apparent to those skilled in the art, in view of the description in this document.

Although the aforementioned description specifically describes a portable medical device for administering insulin to a patient, it should be understood that such a device is only one embodiment of the invention. The device can also include any portable device having a display and a processor and which is capable of remaining in a specific response state while the another operation is being performed on the device. For example, the device can include a mobile computing device, such as a Smartphone. In one embodiment, such a device can be used to remotely control a portable medical device as described herein. Alternatively, a portable medical device as described herein may be controlled by a dedicated remote control specifically designed for use with the device. The response state can be preventing any user input while a user is downloading an application through a wireless connection, or completing a bank transaction, for example.

The methods, systems, and devices discussed above are intended merely to be examples. Various embodiments may omit, substitute, or add various procedures or components as appropriate. For example, it should be appreciated that, in alternative embodiments, the methods may be performed in an order different from that described, and various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in this description to provide a thorough understanding of the embodiments. Nevertheless, it will be understood by one of ordinary skill in the art that the embodiments may be practiced without these specific details. For example, well-known circuits, processes, algorithms, structures, and techniques have been shown without unnecessary detail in order to avoid obscuring the embodiments. Further, the headings provided herein are intended merely to aid in the clarity of the descriptions of various embodiments, and should not be construed as limiting the scope of the invention or the functionality of any part of the invention. For example, certain methods or components may be implemented as part of other methods or components, even though they are described under different headings.

It is noted that embodiments may have been described as a process that is depicted as a flow diagram or block diagram. Although each diagram may describe the process as a sequential series of operations, many of the operations can be performed in parallel or concurrently. In addition, the order of the operations may be rearranged. A process may have additional steps not included in the figures. Each operation of a process is performed or executed by the processor of the device.

The description above has been provided in terms of presently preferred embodiments so that an understanding of the present invention can be conveyed. There are, however, many configurations and techniques for data management systems that were not specifically described herein, but with which the present invention is applicable. The present invention should therefore not be seen as limited to the particular embodiments described herein, but rather, it should be understood that the present invention has wide applicability with respect to data management generally. All modifications, variations, or equivalent arrangements and implementations that are within the scope of the attached claims should therefore be considered within the scope of the invention.

The invention claimed is:

1. A remote control device for remotely controlling an ambulatory infusion pump, comprising:
   a user interface;
   a processor configured to process input received through the user interface to send at least one operating command to an ambulatory infusion pump in response to the input to remotely control the ambulatory infusion pump, the processor further configured to:
      receive input through the user interface selecting a menu item to initiate a software download on the remote control device from a plurality of menu items displayed on a menu screen on the user interface;
      display a lock screen on the user interface that automatically locks at least one portion of the user interface from receiving input in response to the input selecting the menu item to initiate the software download; and
      following completion of the software download, initiate unlocking of the at least one portion of the user interface upon receiving a predefined unlock input through the lock screen, and wherein following receipt of the predefined unlock input through the lock screen, the processor is configured to display an unlock confirmation screen on the user interface and the at least one portion of the user interface is unlocked when only a single predefined confirmation input is received on the unlock confirmation screen and wherein the single predefined confirmation input is a single predefined touch input provided to confirm the predefined unlock input.

2. The remote control device of claim 1, wherein the user interface and the processor are part of a mobile computing device configured to remotely control the ambulatory infusion pump.

3. The remote control device of claim 2, wherein the mobile computing device is a smartphone.

4. The remote control device of claim 1, wherein the user interface and the processor are part of a dedicated remote controller designed for use with a type of the ambulatory infusion pump.

5. The remote control device of claim 1, wherein automatically locking at least one portion of the user interface from receiving input includes locking the user interface from receiving any input other than the predefined unlock input.

6. The remote control device of claim 1, wherein the user interface includes an interactive display.

7. The remote control device of claim 6, wherein the interactive display is a touchscreen.

8. The remote control device of claim 1, wherein the menu item identifies the operation that is to be performed on the remote control device.

9. A remote control device for remotely controlling an ambulatory infusion pump, comprising:
an interactive display;
a processor configured to:
present a user interface for remote control of the ambulatory infusion pump on the interactive display;
process input received on the interactive display to navigate among menu screens on the user interface;
transmit operating commands to the ambulatory infusion pump in response to input on the menu screens;
receive input through the interactive display selecting a menu item on one of the menu screens to initiate a software download on the remote control device;
display a lock screen on the interactive display that automatically locks the interactive display from receiving input to navigate among menu screens while the software download is performed on the remote control device in response to the input selecting the menu item to initiate the software download, the lock screen informing a user that the interactive display is locked; and
initiate unlocking of the interactive display following completion of the software download upon receiving a predefined unlock input through the lock screen, and
wherein following receipt of the predefined unlock input through the lock screen the processor is configured to display an unlock confirmation screen on the interactive display and the interactive display is unlocked when only a single predefined confirmation input is received on the unlock confirmation screen, and wherein the single predefined confirmation input is a single predefined touch input provided to confirm the predefined unlock input.

10. The remote control device of claim 9, wherein the interactive display and the processor are part of a mobile computing device configured to remotely control the ambulatory infusion pump.

11. The remote control device of claim 10, wherein the mobile computing device is a smartphone.

12. The remote control device of claim 9, wherein the interactive display and the processor are part of a dedicated remote controller designed for use with a type of the ambulatory infusion pump.

13. The remote control device of claim 9, wherein automatically locking the interactive display from receiving input to navigate among menu screens while the operation is performed on the remote control device includes locking the interactive display from receiving any input other than the predefined unlock input.

14. The remote control device of claim 9, wherein the interactive display is a touchscreen.

15. A method of remotely controlling an ambulatory infusion pump, comprising:
presenting a user interface for remote control of the ambulatory infusion pump on a remote control device;
processing input received on the user interface to navigate among menu screens on the remote control device;
transmitting operating commands to the ambulatory infusion pump in response to input entered via the menu screens;
receiving input through the user interface selecting a menu item on one of the menu screens to initiate a software download on the remote control device;
in response to the input selecting the menu item to initiate a software download on the remote control device, displaying a lock screen on the user interface that automatically locks the user interface from receiving input to navigate among menu screens while the software download is performed on the remote control device and informs a user that the user interface is locked; and
initiating unlocking the user interface following completion of the software download,
upon receiving a predefined unlock input through the lock screen, and
following receipt of the predefined unlock input through the lock screen, displaying an unlock confirmation screen on the user interface and the user interface is unlocked when only a single predefined confirmation input is received on the unlock confirmation screen and wherein the single predefined confirmation input is a single predefined touch input provided to confirm the predefined unlock input.

16. The method of claim 15, wherein the remote control device is selected from the set consisting of a mobile computing device and a dedicated remote controller.

* * * * *